United States Patent
Woo et al.

(10) Patent No.: US 10,036,046 B2
(45) Date of Patent: Jul. 31, 2018

(54) **TRANSFORMED *SYNECHOCOCCUS ELONGATUS* HAVING CAPABILITY OF PRODUCING BIODIESEL FROM CARBON DIOXIDE AND METHOD FOR PRODUCING BIODIESEL USING THE SAME**

(71) Applicant: Korea Institute of Science and Technology, Seoul (KR)

(72) Inventors: Han Min Woo, Seoul (KR); Hyun Jeong Lee, Seoul (KR); Youngsoon Um, Seoul (KR); Gyeong Taek Gong, Seoul (KR); Sun Mi Lee, Seoul (KR); Yunje Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/299,188

(22) Filed: Oct. 20, 2016

(65) Prior Publication Data

US 2017/0114375 A1    Apr. 27, 2017

(30) Foreign Application Priority Data

Oct. 22, 2015    (KR) .......................... 10-2015-0147216

(51) Int. Cl.
| | | |
|---|---|---|
| *C12N 1/20* | (2006.01) | |
| *C12N 15/70* | (2006.01) | |
| *C12P 7/64* | (2006.01) | |
| *C07H 21/04* | (2006.01) | |
| *C12N 9/04* | (2006.01) | |
| *C12N 9/10* | (2006.01) | |
| *C12N 9/16* | (2006.01) | |
| *C12N 9/88* | (2006.01) | |
| *C12N 15/52* | (2006.01) | |

(52) U.S. Cl.
CPC ............ *C12P 7/649* (2013.01); *C12N 9/0006* (2013.01); *C12N 9/1029* (2013.01); *C12N 9/16* (2013.01); *C12N 9/88* (2013.01); *C12N 15/52* (2013.01); *C12Y 101/01001* (2013.01); *C12Y 401/01001* (2013.01)

(58) Field of Classification Search
None
See application file for complete search history.

(56) References Cited

U.S. PATENT DOCUMENTS 8,652,815 B2    2/2014   Han et al.

FOREIGN PATENT DOCUMENTS

| KR | 10-2008-0113199 A | 12/2008 |
|---|---|---|
| KR | 10-2010-0015763 A | 2/2010 |
| KR | 10-1349295 B1 | 1/2014 |
| WO | WO 2007/084477 A1 | 7/2007 |
| WO | WO 2008/119082 A2 | 10/2008 |

OTHER PUBLICATIONS

Ruffing et al. Physiological Effects of Free Fatty Acid Production in Genetically Engineered Synechococcus elongatus PCC 7942, Biotechnology and Bioengineering (2012), 109: 2190-2199.*
Steen, Eric J., et al. "Microbial Production of Fatty-Acid Derived Fuels and Chemicals from Plant Biomass." Nature 463.7280 (2010): 559-562. (5 pages, in English).
Thompson, R. Adam, and Cong T. Trinh. "Enhancing Fatty Acid Ethyl Ester Production in *Saccharomyces cerevisiae* Through Metabolic Engineering and Medium Optimization." Biotechnology and Bioengineering 111.11 (2014): 2200-2208. (9 pages in English).
Voshol, Gerben. *Biodiesel Production Using Blue-Green Cyanobacterium Synechococcus elongatus PCC 7942*. Diss. Department of Molecular Microbiology and Biotechnology, Institute of Biology, Faculty of Science, Leiden University, 2015, (112 pages, in English).

* cited by examiner

*Primary Examiner* — Iqbal H Chowdhury
(74) *Attorney, Agent, or Firm* — NSIP Law

(57) ABSTRACT

The present disclosure discloses a transformed *Synechococcus elongatus* strain capable of producing biodiesel directly from carbon dioxide and a method for producing biodiesel and a method for removing carbon dioxide using the same. In an aspect, the transformed *Synechococcus elongatus* strain of the present disclosure can produce biodiesel in large scale using carbon dioxide as a carbon source. The *Synechococcus elongatus* strain is environment-friendly because it can be used to remove or reduce carbon dioxide in the atmosphere. The strain of the present disclosure is advantageous in that it can produce biodiesel in large scale because it grows faster and exhibits excellent carbon dioxide fixation capability as compared to other photosynthetic microorganisms.

16 Claims, 12 Drawing Sheets

Module A: NSII::ZmPdc-ZmAdhB
Module B: NSI:: AbAftA
Module C: ΔfadE::Ec'tesA

SEQUENCE LISTING

```
<160> NUMBER OF SEQ ID NOS: 9

<210> SEQ ID NO 1
<211> LENGTH: 1707
<212> TYPE: DNA
<213> ORGANISM: Artificial Sequence
<220> FEATURE:
<223> OTHER INFORMATION: pdc gene

<400> SEQUENCE: 1
atgagctaca ccgtgggcac ctacctggcc gaacgcctgg tgcagatcgg cctgaaacac      60
cactttgccg tggccggcga ttacaacctg gtgctgctga taacctgct gctgaacaaa      120 aacatggaac aggtgtactg ctgcaacgaa ctgaactgcg gctttagcgc cgaaggctac     180
gcccgcgcca aggcgccgc cgccgccgtg gtgacctaca gcgtgggcgc cctgagcgcc      240
tttgatgcca tcggcggcgc ctacgccgaa aacctgcccg tgatcctgat cagcggcgcc     300
cccaacaaca acgatcacgc cgccggccac gtgctgcacc acgccctggg caaaaccgat     360
taccactacc agctggaaat ggccaaaaac atcaccgccg ccgccgaagc catctacacc     420
cccgaagaag cccccgccaa aatcgatcac gtgatcaaaa ccgccctgcg cgaaaaaaaa     480
cccgtgtacc tggaaatcgc ctgcaacatc gccagcatgc cctgcgccgc ccccggcccc    540
gccagcgccc tgtttaacga tgaagccagc gatgaagcca gcctgaacgc cgccgtggaa    600
gaaaccctga aatttatcgc caaccgcgat aaagtggccg tgctggtggg cagcaaactg    660
cgcgccgccg gcgccgaaga agccgccgtg aaatttgccg atgccctggg cggcgccgtg   720
gccaccatgg ccgccgccaa aagcttttt cccgaagaaa accccacta catcggcacc       780 agctggggcg aagtgagcta ccccggcgtg gaaaaaacca tgaaagaagc cgatgccgtg    840
atcgccctgg ccccgtgtt taacgattac agcaccaccg gctggaccga tatccccgat    900
cccaaaaaac tggtgctggc cgaaccccgc agcgtggtgg tgaacggcat ccgctttccc     960
agcgtgcacc tgaaagatta cctgacccgc ctggcccaga aagtgagcaa aaaaaccggc    1020
gccctggatt tttttaaaag cctgaacgcc ggcgaactga aaaagccgc cccgccgat    1080 cccagcgccc cctggtgaa cgccgaaatc gcccgccagg tggaagccct gctgaccccc    1140
aacaccaccg tgatcgccga aaccggcgat agctggttta cgcccagcg catgaaactg     1200 cccaacggcg cccgcgtgga atacgaaatg cagtggggcc acatcggctg gagcgtgccc   1260
gccgcctttg gctacgccgt gggcgccccc gaacgccgca acatcctgat ggtgggcgat   1320
ggcagctttc agctgaccgc ccaggaagtg gcccagatgg tgcgcctgaa actgcccgtg   1380
```

| | |
|---|---|
| atcatctttc tgatcaacaa ctacggctac accatcgaag tgatgatcca cgatggcccc | 1440 |
| tacaacaaca tcaaaaactg ggattacgcc ggcctgatgg aagtgtttaa cggcaacggc | 1500 |
| ggctacgata gcggcgccgg caaaggcctg aaagccaaaa ccggcggcga actggccgaa | 1560 |
| gccatcaaag tggccctggc caacaccgat ggccccaccc tgatcgaatg ctttatcggc | 1620 |
| cgcgaagatt gcaccgaaga actggtgaaa tggggcaaac gcgtggccgc cgccaacagc | 1680 |
| cgcaaacccg tgaacaaact gctgtag | 1707 |

<210> SEQ ID NO 2
<211> LENGTH: 1152
<212> TYPE: DNA
<213> ORGANISM: Artificial Sequence
<220> FEATURE:
<223> OTHER INFORMATION: adh gene

<400> SEQUENCE: 2

| | |
|---|---|
| atggccagca gcacctttta catccccttt gtgaacgaaa tgggcgaagg cagcctggaa | 60 |
| aaagccatca agacctgaa cggcagcggc tttaaaaacg ccctgatcgt gagcgatgcc | 120 |
| tttatgaaca aaagcggcgt ggtgaaacag gtggccgatc tgctgaaagc ccagggcatc | 180 |
| aacagcgccg tgtacgatgg cgtgatgccc aaccccaccg tgaccgccgt gctggaaggc | 240 |
| ctgaaaatcc tgaaagataa caacagcgat tttgtgatca gcctgggcgg cggcagcccc | 300 |
| cacgattgcg ccaaagccat cgccctggtg gccaccaacg gcggcgaagt gaaagattac | 360 |
| gaaggcatcg ataaaagcaa aaaacccgcc ctgccccctga tgagcatcaa caccaccgcc | 420 |
| ggcaccgcca gcgaaatgac cgctttttgc atcatcaccg atgaagtgcg ccacgtgaaa | 480 |
| atggccatcg tggatcgcca cgtgaccccc atggtgagcg tgaacgatcc cctgctgatg | 540 |
| gtgggcatgc ccaaaggcct gaccgccgcc accggcatgg atgccctgac ccacgccttt | 600 |
| gaagcctaca gcagcaccgc cgccaccccc atcaccgatg cctgcgccct gaaagccgcc | 660 |
| agcatgatcg ccaaaaacct gaaaaccgcc tgcgataacg gcaaagatat gcccgcccgc | 720 |
| gaagccatgg cctacgccca gtttctggcc ggcatggcct taacaacgc cagcctgggc | 780 |
| tacgtgcacg ccatggccca ccagctgggc ggctactaca acctgccccca cggcgtgtgc | 840 |
| aacgccgtgc tgctgcccca cgtgctggcc tacaacgcca gcgtggtggc cggccgcctg | 900 |
| aaagatgtgg gcgtggccat gggcctggat atcgccaacc tgggcgataa agaaggcgcc | 960 |
| gaagccacca tccaggccgt gcgcgatctg gccgccagca tcggcatccc cgccaacctg | 1020 |
| accgaactgg cgccaaaaa agaagatgtg cccctgctgg ccgatcacgc cctgaaagat | 1080 |
| gcctgcgccc tgaccaaccc ccgccagggc gatcagaaag aagtggaaga actgtttctg | 1140 |
| agcgcctttt ag | 1152 |

<210> SEQ ID NO 3
<211> LENGTH: 1377
<212> TYPE: DNA
<213> ORGANISM: Artificial Sequence
<220> FEATURE:
<223> OTHER INFORMATION: atfA gene

<400> SEQUENCE: 3

| | |
|---|---|
| atgcgccccc tgcaccccat cgattttatc tttctgagcc tggaaaaacg ccagcagccc | 60 |
| atgcacgtgg gcggcctgtt tctgtttcag atcccgata cgcccccga tacctttatc | 120 |
| caggatctgg tgaacgatat ccgcatcagc aaaagcatcc ccgtgccccc ctttaacaac | 180 |
| aaactgaacg gcctgttttg ggatgaagat gaagaatttg atctggatca ccacttttgc | 240 |

| | |
|---|---|
| cacatcgccc tgccccaccc cggccgcatc cgcgaactgc tgatctacat cagccaggaa | 300 |
| cacagcaccc tgctggatcg cgccaaaccc ctgtggacct gcaacatcat cgaaggcatc | 360 |
| gaaggcaacc gctttgccat gtactttaaa atccaccacg ccatggtgga tggcgtggcc | 420 |
| ggcatgcgcc tgatcgaaaa aagcctgagc acgatgtga ccgaaaaaag catcgtgccc | 480 |
| ccctggtgcg tggaaggcaa acgcgccaaa cgcctgcgcg aacccaaaac cggcaaaatc | 540 |
| aaaaaaatca tgagcggcat caaaagccag ctgcaggcca cccccaccgt gatccaggaa | 600 |
| ctgagccaga ccgtgtttaa agatatcggc cgcaaccccg atcacgtgag cagctttcag | 660 |
| gcccctgca gcatcctgaa ccagcgcgtg agcagcagcc gccgctttgc cgcccagagc | 720 |
| tttgatctgg atcgctttcg caacatcgcc aaaagcctga acgtgaccat caacgatgtg | 780 |
| gtgctggccg tgtgcagcgg cgccctgcgc gcctacctga tgagccacaa cagcctgccc | 840 |
| agcaaacccc tgatcgccat ggtgcccgcc agcatccgca cgatgatag cgatgtgagc | 900 |
| aaccgcatca ccatgatcct ggccaacctg gccacccaca agatgatcc cctgcagcgc | 960 |
| ctggaaatca tccgccgcag cgtgcagaac agcaaacagc gctttaaacg catgaccagc | 1020 |
| gatcagatcc tgaactacag cgccgtggtg tacggccccg ccggcctgaa catcatcagc | 1080 |
| ggcatgatgc ccaaacgcca ggcctttaac ctggtgatca gcaacgtgcc cggccccgc | 1140 |
| gaacccctgt actggaacgg cgccaaactg gatgccctgt accccgccag catcgtgctg | 1200 |
| gatggccagg ccctgaacat caccatgacc agctacctgg ataaactgga agtgggcctg | 1260 |
| atcgcctgcc gcaacgccct gccccgcatg cagaacctgc tgacccacct ggaagaagaa | 1320 |
| atccagctgt ttgaaggcgt gatcgccaaa caggaagata tcaaaaccgc caactag | 1377 |

```
<210> SEQ ID NO 4
<211> LENGTH: 1422
<212> TYPE: DNA
<213> ORGANISM: Artificial Sequence
<220> FEATURE:
<223> OTHER INFORMATION: ws2 gene

<400> SEQUENCE: 4
```

| | |
|---|---|
| atgaaacgcc tgggcaccct ggatgccagc tggctggccg tggaaagcga agataccccc | 60 |
| atgcacgtgg gcaccctgca gattttagc ctgcccgaag gcgcccccga aacctttctg | 120 |
| cgcgatatgg tgacccgcat gaaagaagcc ggcgatgtgg ccccccctg ggctacaaa | 180 |
| ctggcctgga gcggctttct gggccgcgtg atcgcccccg cctggaaagt ggataaagat | 240 |
| atcgatctgg attaccacgt gcgccacagc gccctgcccc gccccggcgg cgaacgcgaa | 300 |
| ctgggcatcc tggtgagccg cctgcacagc aaccccctgg attttagccg cccctgtgg | 360 |
| gaatgccacg tgatcgaagg cctggaaaac aaccgctttg ccctgtacac caaaatgcac | 420 |
| cacagcatga tcgatggcat cagcggcgtg cgcctgatgc agcgcgtgct gaccaccgat | 480 |
| cccgaacgct gcaacatgcc cccccctgg accgtgcgcc ccaccagcg ccgcggcgcc | 540 |
| aaaaccgata agaagccag cgtgcccgcc gccgtgagcc aggccatgga tgccctgaaa | 600 |
| ctgcaggccg atatggcccc ccgcctgtgg caggccggca accgcctggt gcacagcgtg | 660 |
| cgccaccccg aagatggcct gaccgccccc tttaccggcc ccgtgagcgt gctgaaccac | 720 |
| cgcgtgaccg cccagcgccg ctttgccacc cagcactacc agctggatcg cctgaaaaac | 780 |
| ctgcccacg ccagcggcgg cagcctgaac gatatcgtgc tgtacctgtg cggcaccgcc | 840 |
| ctgcgccgct ttctgccga acagaacaac ctgcccgata cccccctgac cgccggcatc | 900 |
| cccgtgaaca tccgccccgc cgatgatgaa ggcaccggca cccagatcag ctttatgatc | 960 |

```
gccagcctgg ccaccgatga agccgatccc ctgaaccgcc tgcagcagat caaaaccagc    1020
acccgccgcg ccaaagaaca cctgcagaaa ctgcccaaaa gcgccctgac ccagtacacc    1080
atgctgctga tgagccccta catcctgcag ctgatgagcg gctgggcgg ccgcatgcgc    1140 cccgtgttta acgtgaccat cagcaacgtg cccggcccg aaggcaccct gtactacgaa    1200
ggcgcccgcc tggaagccat gtaccccgtg agcctgatcg cccacggcgg cgccctgaac    1260
atcacctgcc tgagctacgc cggcagcctg aactttggct ttaccggctg ccgcgatacc    1320
ctgcccagca tgcagaaact ggccgtgtac accggcgaag ccctggatga actggaaagc    1380
ctgatcctgc ccccaaaaa acgcgcccgc acccgcaaat ag                        1422

<210> SEQ ID NO 5
<211> LENGTH: 552
<212> TYPE: DNA
<213> ORGANISM: Artificial Sequence
<220> FEATURE:
<223> OTHER INFORMATION: tesA gene

<400> SEQUENCE: 5
atggccgata ccctgctgat cctgggcgat agcctgagcg ccggctaccg catgagcgcc      60
agcgccgcct ggccccgccct gctgaacgat aaatggcaga gcaaaaccag cgtggtgaac    120
gccagcatca gcggcgatac cagccagcag ggcctggccc gcctgccgc cctgctgaaa     180 cagcaccagc cccgctgggt gctggtggaa ctgggcggca acgatggcct gcgcggcttt    240
cagccccagc agaccgaaca gaccctgcgc cagatcctgc aggatgtgaa agccgccaac    300
gccgaacccc tgctgatgca gatccgcctg cccgccaact acggccgccg ctacaacgaa    360
gcctttagcg ccatctaccc caaactggcc aaagaatttg atgtgcccct gctgcccttt    420
tttatggaag aagtgtacct gaaacccag tggatgcagg atgatggcat ccaccccaac    480
cgcgatgccc agccctttat cgccgattgg atggccaaac agctgcagcc cctggtgaac    540
cacgatagct ag                                                         552

<210> SEQ ID NO 6
<211> LENGTH: 8148
<212> TYPE: DNA
<213> ORGANISM: Artificial Sequence
<220> FEATURE:
<223> OTHER INFORMATION: pSe2Bb1k-pdc,adh vector

<400> SEQUENCE: 6
gataatctca tgaccaaaat cccttaacgt gagttttcgt tccactgagc gtcagacccc      60
gtagaaaaga tcaaaggatc ttcttgagat cctttttttc tgcgcgtaat ctgctgcttg    120
caaacaaaaa aaccaccgct accagcggtg gtttgtttgc cggatcaaga gctaccaact    180 cttttttccga aggtaactgg cttcagcaga gcgcagatac caaatactgt tcttctagtg    240
tagccgtagt taggccacca cttcaagaac tctgtagcac cgcctacata cctcgctctg    300
ctaatcctgt taccagtggc tgctgccagt ggcgataagt cgtgtcttac cgggttggac    360
tcaagacgat agttaccgga taaggcgcag cggtcgggct gaacggggg ttcgtgcaca    420 cagcccagct tggagcgaac gacctacacc gaactgagat acctacagcg tgagctatga    480
gaaagcgcca cgcttcccga agggagaaag gcggacaggt atccggtaag cggcagggtc    540
ggaacaggag agcgcacgag ggagcttcca gggggaaacg cctggtatct ttatagtcct    600
gtcgggtttc gccacctctg acttgagcgt cgatttttgt gatgctcgtc aggggggcgg    660
agcctatgga aaaacgccag caacgcggcc ttttttacggt tcctggcctt tgctggcct    720
```

```
tttgctcaca tgtgtgctgg gccctaagcg ggccacggca gcgaaagggc gacggcgcga    780
tcgccggtat ggaaaacgct tgctgcagca tcagatcgat gcgatcgccg aagactgtga    840
cctagatgag gaagcatgag cgaactgggc ttgagtctga cggcgatcgc gattttacc     900
acgacggcat tagctttggt gggaccaatg ctgggtagtt ctccgctgct accggcggga    960
ttgggttta gcctcttggt gctgttcagt ctggatgcgg tgacttggca ggggcggggt    1020
gccacgttac tgctcgatgg cattcagcag cgatcgcccg aatatcgtca gcggattttg   1080
catcacgaag cgggtcacta cttggtagca accgcgctgg ggttacccgt gacgggctac   1140
accctctcag cgtgggaagc gctgcgccaa ggacaacctg gtcgcggggg tgtgcagttc   1200
caagcagctg cgctagaagc cgaagccgca caggggcaac tcagtcagcg atcgctggaa   1260
cagtggtgtc aggtgttgat ggccggtgca gcggcagagc aactggtcta cggcaacgtg   1320
gaagggggag ctgacgatcg cgcccagtgg aaacaactgt ggcggcaact cgatcgcaat   1380
cctgccgaag cggatttacg cagtcgctgg ggattgttac gggcgaagac tttactggag   1440
caacaacgtc ccgcctacga tgcttttggtg gcggcgatgg ctgcagaggc cagcattgaa   1500
gactgcaatc aagcgatcgc cactgcttgg gtagaagaac ctgcgatcgc gcttagtga    1560
agagtccaga agattcccct cccctctcgc ccaatggaca agggaaatgt gattcagcat   1620
gagtcaagtc cccagtgcat ggatgggtgt gcaatgagag ctctcgaacc ccagagtccc   1680
gctcagaaga actcgtcaag aaggcgatag aaggcgatgc gctgcgaatc gggagcggcg   1740
ataccgtaaa gcacgaggaa gcggtcagcc cattcgccgc caagctcttc agcaatatca   1800
cgggtagcca acgctatgtc ctgatagcgg tccgccacac ccagccggcc acagtcgatg   1860
aatccagaaa agcggccatt ttccaccatg atattcggca agcaggcatc gccatgggtc   1920
acgacgagat cctcgccgtc gggcatgcgc gccttgagcc tggcgaacag ttcggctggc   1980
gcgagcccct gatgctcttc gtccagatca tcctgatcga caagaccggc ttccatccga   2040
gtacgtgctc gctcgatgcg atgtttcgct tggtggtcga atgggcaggt agccggatca   2100
agcgtatgca gccgccgcat tgcatcagcc atgatggata cttttctcggc aggagcaagg   2160
tgagatgaca ggagatcctg ccccggcact tcgcccaata gcagccagtc ccttcccgct   2220
tcagtgacaa cgtcgagcac agctgcgcaa ggaacgcccg tcgtggccag ccacgatagc   2280
cgcgctgcct cgtcctgcag ttcattcagg caccggaca ggtcggtctt gacaaaaaga    2340
accgggcgcc cctgcgctga cagccggaac acggcggcat cagagcagcc gattgtctgt   2400
tgtgcccagt catagccgaa tagcctctcc acccaagcgg ccgagaaacc tgcgtgcaat   2460
ccatcttgtt caatcatgcg aaacgatcct catcctgtct cttgatcaga tcatgatccc   2520
ctgcgccatc agatccttgg cggcaagaaa gccatccagt ttactttgca gggcttccca   2580
accttaccag agggcgcccc agctggcaat tccgacgtcg acaccatcga atggtgcaaa   2640
accttcgcg gtatggcatg atagcgcccg gaagagagtc aattcagggt ggtgaatgtg   2700
aaaccagtaa cgttatacga tgtcgcagag tatgccggtg tctcttatca gaccgtttcc   2760
cgcgtggtga accaggccag ccacgtttct gcgaaaacgc gggaaaaagt ggaagcggcg   2820
atggcggagc tgaattacat tcccaaccgc gtggcacaac aactggcggg caaacagtcg   2880
ttgctgattg gcgttgccac ctccagtctg gccctgcacg cgccgtcgca aattgtcgcg   2940
gcgattaaat ctcgcgccga tcaactgggt gccagcgtgg tggtgtcgat ggtagaacga   3000
agcggcgtca agcctgtaa agcggcggtg cacaatcttc tcgcgcaacg cgtcagtggg   3060
ctgatcatta actatccgct ggatgaccag gatgccattg ctgtggaagc tgcctgcact   3120
```

```
aatgttccgg cgttatttct tgatgtctct gaccagacac ccatcaacag tattattttc   3180
tcccatgaag acggtacgcg actgggcgtg gagcatctgg tcgcattggg tcaccagcaa   3240
atcgcgctgt tagcgggccc attaagttct gtctcggcgc gtctgcgtct ggctggctgg   3300
cataaatatc tcactcgcaa tcaaattcag ccgatagcgg aacgggaagg cgactggagt   3360
gccatgtccg gttttcaaca aaccatgcaa atgctgaatg agggcatcgt tcccactgcg   3420
atgctggttg ccaacgatca gatggcgctg ggcgcaatgc gcgccattac cgagtccggg   3480
ctgcgcgttg gtgcggatat ctcggtagtg ggatacgacg ataccgaaga cagctcatgt   3540
tatatcccgc cgttaaccac catcaaacag gattttcgcc tgctggggca aaccagcgtg   3600
gaccgcttgc tgcaactctc tcagggccag gcggtgaagg gcaatcagct gttgcccgtc   3660
tcactggtga aaagaaaaac caccctggcg cccaatacgc aaaccgcctc tccccgcgcg   3720
ttggccgatt cattaatgca gctggcacga caggtttccc gactggaaag cgggcagtga   3780
gcgcaacgca attaatgtaa gttagcgcga attgatctgg tttgacagct tatcatcgac   3840
tgcacggtgc accaatgctt ctggcgtcag gcagccatcg gaagctgtgg tatggctgtg   3900
caggtcgtaa atcactgcat aattcgtgtc gctcaaggcg cactcccgtt ctggataatg   3960
ttttttgcgc cgacatcata acggttctgg caaatattct gaaatgagct gttgacaatt   4020
aatcatccgg ctcgtataat gtgtggaatt gtgagcggat aacaatttca gaattcaaaa   4080
gatctaatca ccccaccgcc taagatagag acgagacgca atgagctaca ccgtgggcac   4140
ctacctggcc gaacgcctgg tgcagatcgg cctgaaacac cactttgccg tggccggcga   4200
ttacaacctg gtgctgctgg ataacctgct gctgaacaaa acatggaac aggtgtactg   4260 ctgcaacgaa ctgaactgcg gctttagcgc cgaaggctac gcccgcgcca aaggcgccgc   4320
cgccgccgtg gtgaccctaca gcgtgggcgc cctgagcgcc tttgatgcca tcggcggcgc   4380
ctacgccgaa aacctgcccg tgatcctgat cagcggcgcc cccaacaaca cgatcacgc   4440 cgccggccac gtgctgcacc acgccctggg caaaaccgat taccactacc agctggaaat   4500
ggccaaaaac atcaccgccg ccgccgaagc catctacacc cccgaagaag ccccgccaa   4560 aatcgatcac gtgatcaaaa ccgccctgcg cgaaaaaaaa cccgtgtacc tggaaatcgc   4620
ctgcaacatc gccagcatgc cctgcgccgc ccccggcccc gccagcgccc tgtttaacga   4680
tgaagccagc gatgaagcca gcctgaacgc cgccgtggaa gaaaccctga aattatcgc   4740 caaccgcgat aaagtggccg tgctggtggg cagcaaactg cgcgccgccg cgccgaaga   4800 agccgccgtg aaattgcccg atgccctggg cggcgccgtg gccaccatgg ccgccgccaa   4860 aagcttttt cccgaagaaa accccacta catcggcacc agctggggcg aagtgagcta   4920
ccccggcgtg gaaaaaacca tgaaagaagc cgatgccgtg atcgccctgg cccccgtgtt   4980
taacgattac agcaccaccg gctggaccga tatccccgat cccaaaaaac tggtgctggc   5040 cgaacccgc agcgtggtgg tgaacggcat ccgctttccc agcgtgcacc tgaaagatta   5100 cctgaccgc ctggcccaga aagtgagcaa aaaaccggc gccctggatt tttttaaaag   5160
cctgaacgcc ggcgaactga aaaagccgc cccgccgat ccagcgccc cctggtgaa   5220 cgccgaaatc gcccgccagg tggaagccct gctgaccccc aacaccaccg tgatcgccga   5280
aaccggcgat agctggttta cgccagcg catgaaactg cccaacggcg cccgcgtgga   5340
atacgaaatg cagtggggcc acatcggctg gagcgtgccc gccgcctttg gctacgccgt   5400
gggcgccccc gaacgccgca acatcctgat ggtgggcgat ggcagctttc agctgaccgc   5460
ccaggaagtg gcccagatgg tgcgcctgaa actgcccgtg atcatctttc tgatcaacaa   5520
```

```
ctacggctac accatcgaag tgatgatcca cgatggcccc tacaacaaca tcaaaaactg    5580
ggattacgcc ggcctgatgg aagtgtttaa cggcaacggc ggctacgata gcggcgccgg    5640
caaaggcctg aaagccaaaa ccggcggcga actggccgaa gccatcaaag tggccctggc    5700
caacaccgat ggccccaccc tgatcgaatg ctttatcggc cgcgaagatt gcaccgaaga    5760
actggtgaaa tggggcaaac gcgtggccgc cgccaacagc cgcaaacccg tgaacaaact    5820
gctgtaggga tcttcgatct acaaaccgta aagtcgagac atcgaagaat ggccagcagc    5880
accttttaca tccccttgt gaacgaaatg ggcgaaggca gcctggaaaa agccatcaaa     5940
gacctgaacg gcagcggctt taaaaacgcc ctgatcgtga cgatgccctt tatgaacaaa    6000
agcggcgtgg tgaaacaggt ggccgatctg ctgaaagccc agggcatcaa cagcgccgtg    6060
tacgatggcg tgatgcccaa ccccaccgtg accgccgtgc tggaaggcct gaaaatcctg    6120
aaagataaca acagcgattt tgtgatcagc ctgggcggcg gcagccccca cgattgcgcc    6180
aaagccatcg ccctggtggc caccaacggc ggcgaagtga agattacgca aggcatcgat    6240
aaaagcaaaa aacccgccct gccccctgatg agcatcaaca ccaccgccgg caccgccagc    6300
gaaatgaccc gcttttgcat catcaccgat gaagtgcgcc acgtgaaaat ggccatcgtg    6360
gatcgccacg tgaccccat ggtgagcgtg aacgatcccc tgctgatggt gggcatgccc     6420
aaaggcctga ccgccgccac cggcatggat gccctgaccc acgcctttga agcctacagc    6480
agcaccgccg ccacccccat caccgatgcc tgcgccctga agccgccag catgatcgcc     6540
aaaaacctga aaccgcctg cgataacggc aaagatatgc ccgcccgcga agccatggcc    6600
tacgcccagt ttctggccgg catggccttt aacaacgcca gctgggcta cgtgcacgcc    6660
atggcccacc agctgggcgg ctactacaac ctgccccacg gcgtgtgcaa cgccgtgctg    6720
ctgccccacg tgctggccta caacgccagc gtggtggccg ccgcctgaa agatgtgggc     6780
gtggccatgg gcctggatat cgccaacctg gcgataaag aaggcgccga agccaccatc    6840
caggccgtgc gcgatctggc cgccagcatc ggcatccccg ccaacctgac cgaactgggc    6900
gccaaaaaag aagatgtgcc cctgctggcc gatcacgccc tgaaagatgc ctgcgccctg    6960
accaaccccc gccagggcga tcagaaagaa gtggaagaac tgtttctgag cgccttttag    7020
ggatccaaac tcgagtaagg atctccaggc atcaaataaa acgaaaggct cagtcgaaag    7080
actgggcctt tcgttttatc tgttgtttgt cggtgaacgc tctctactag agtcacactg    7140
gctcaccttc gggtgggcct ttctgcgttt atacctaggg cgttcggctg cggcgagcgg    7200
tatcagctca ctcaaaggcg gtaatacggg caattcaaga gcatccaaag cctcttcaac    7260
cccaggaacg gcttgtagat gcgtttctaa cgcgatacgg gtacggcgtt gatagtgctg    7320
aacaaagtca gggggtggag gattgcctaa ccgtcgctca attagtttga gacagtcagc    7380
catggaatga cccacaaact gctcaaacat gtcatccaaa gtcaccaaca gacccagttc    7440
attgagcatg tctgcaaaga cgcgattagt gatgcgttcg ctatcaacaa gcacaccatc    7500
acagtcgaaa atcaccagct gaaacggtga agtttgcatt gttttaagc acgagccatc    7560
aacagtaaga gcgatcgcgc tgggacgatg taatcgcgcc gtaggcaggg ttttgcctca    7620
tccggcagat gacaagcttc aagattcggc agtgaagtat cgagcaagcg ataccaaacg    7680
cggccgcgag gaggcctcgg caactggaag cgcaggtctt cccagtaagc attaaaggct    7740
aggtaaagcc attcctgctg gcgaggatgg cagagactga cggccagact gtgggaccac    7800
agcgcccaat cgggttgttt gagtttgacg ccatgccaga tggcataggg acgacgcgga    7860
tggggttcgt tctgcagcag ttcgttctgt tggaacatca ccagcgactg ggaaagttca    7920
```

| | |
|---|---:|
| atcaggcggc gactgaacac caagaaatcg gcatggcgat cgcacagcga ccaatcaaac | 7980 |
| cagctgatct cattgtcttg gcagtaggcg ttattgttac cctgctgact gcgtttgacc | 8040 |
| tcatcgccca tcgtcagcat cggtgtgccc tgggcgagga ataacgtggc gagcaaattg | 8100 |
| cgctgctgcc gttcccgtaa gctcagaatc gtggggtcat cggtctcg | 8148 |

<210> SEQ ID NO 7
<211> LENGTH: 6580
<212> TYPE: DNA
<213> ORGANISM: Artificial Sequence
<220> FEATURE:
<223> OTHER INFORMATION: pSe1Bb1s-atfA vector

<400> SEQUENCE: 7

| | |
|---|---:|
| gataatctca tgaccaaaat cccttaacgt gagttttcgt tccactgagc gtcagacccc | 60 |
| gtagaaaaga tcaaaggatc ttcttgagat cctttttttc tgcgcgtaat ctgctgcttg | 120 |
| caaacaaaaa aaccaccgct accagcggtg gtttgtttgc cggatcaaga gctaccaact | 180 |
| ctttttccga aggtaactgg cttcagcaga gcgcagatac caaatactgt tcttctagtg | 240 |
| tagccgtagt taggccacca cttcaagaac tctgtagcac cgcctacata cctcgctctg | 300 |
| ctaatcctgt taccagtggc tgctgccagt ggcgataagt cgtgtcttac cgggttggac | 360 |
| tcaagacgat agttaccgga taaggcgcag cggtcgggct gaacggggg ttcgtgcaca | 420 |
| cagcccagct tggagcgaac gacctacacc gaactgagat acctacagcg tgagctatga | 480 |
| gaaagcgcca cgcttcccga agggagaaag gcggacaggt atccggtaag cggcagggtc | 540 |
| ggaacaggag agcgcacgag ggagcttcca gggggaaacg cctggtatct ttatagtcct | 600 |
| gtcgggtttc gccacctctg acttgagcgt cgatttttgt gatgctcgtc aggggggcgg | 660 |
| agcctatgga aaaacgccag caacgcggcc ttttacggt tcctggcctt ttgctggcct | 720 |
| tttgctcaca tgtgtgctgg gccccaatgc cttctccaag ggcggcattc ccctgactgt | 780 |
| tgaaggcgtt gccaatatca agattgctgg ggaagaaccg accatccaca acgcgatcga | 840 |
| gcggctgctt ggcaaaaacc gtaaggaaat cgagcaaatt gccaaggaga ccctcgaagg | 900 |
| caacttgcgt ggtgttttag ccagcctcac gccggagcag atcaacgagg acaaaattgc | 960 |
| ctttgccaaa agtctgctgg aagaggcgga ggatgacctt gagcagctgg gtcaagtcct | 1020 |
| cgatacgctg caagtccaga acatttccga tgaggtcggt tatctctcgg ctagtggacg | 1080 |
| caagcagcgg gctgatctgc agcgagatgc ccgaattgct gaagccgatg cccaggctgc | 1140 |
| ctctgcgatc caaacggccg aaaatgacaa gatcacggcc ctgcgtcgga tcgatcgcga | 1200 |
| tgtagcgatc gcccaagccg aggccgagcg ccggattcag gatgcgttga cgcggcgcga | 1260 |
| agcggtggtg gccgaagctg aagcggacat tgctaccgaa gtcgctcgta gccaagcaga | 1320 |
| actccctgtg cagcaggagc ggatcaaaca ggtgcagcag caacttcaag ccgatgtgat | 1380 |
| cgccccagct gaggcagctt gtaaacgggg atcgcggaa gcgcgggggg ccgccgcccg | 1440 |
| tatcgtcgaa gatggaaaag ctcaagcgga agggacccaa cggctggcgg aggcttggca | 1500 |
| gaccgctggt gctaatgccc gcgacatctt cctgctccag aagtctagac cagccaggac | 1560 |
| agaaatgcct cgactcgct gctacccaag gttgccgggt gacgcacacc gtggaaacgg | 1620 |
| atgaaggcac gaacccagtg gacataagcc tgttcggttc gtaagctgta atgcaagtag | 1680 |
| cgtatgcgct cacgcaactg gtccagaacc ttgaccgaac gcagcggtgg taacggcgca | 1740 |
| gtggcggttt tcatggcttg ttatgactgt ttttttgggg tacagtctat gcctcgggca | 1800 |
| tccaagcagc aagcgcgtta cgccgtgggt cgatgtttga tgttatggag cagcaacgat | 1860 |

```
gttacgcagc agggcagtcg ccctaaaaca aagttaaaca ttatgaggga agcggtgatc      1920
gccgaagtat cgactcaact atcagaggta gttggcgtca tcgagcgcca tctcgaaccg      1980
acgttgctgg ccgtacattt gtacggctcc gcagtggatg gcggcctgaa gccacacagt      2040
gatattgatt tgctggttac ggtgaccgta aggcttgatg aaacaacgcg gcgagctttg      2100
atcaacgacc ttttggaaac ttcggcttcc cctggagaga gcgagattct ccgcgctgta      2160
gaagtcacca ttgttgtgca cgacgacatc attccgtggc gttatccagc taagcgcgaa      2220
ctgcaatttg gagaatggca cgcaatgac attcttgctg gtatcttcga gccagccacg       2280
atcgacattg atctggctat cttgctgaca aaagcaagag aacatagcgt tgccttggta      2340
ggtccagcgg cggaggaact ctttgatccg gttcctgaac aggatctatt tgaggcgcta      2400
aatgaaacct taacgctatg gaactcgccc cccgactggg ctggcgatga gcgaaatgta      2460
gtgcttacgt tgtcccgcat ttggtacagc gcagtaaccg gcaaaatcgc gccgaaggat      2520
gtcgctgccg actgggcaat ggagcgcctg ccggcccagt atcagcccgt catacttgaa      2580
gctagacagg cttatcttgg acaagaagaa gatcgcttgg cctcgcgcgc agatcagttg      2640
gaagaatttg tccactacgt gaaaggcgag atcaccaagg tagtcggcaa ataacctcat      2700
tttcgccaga tatcgacgtc gacaccatcg aatggtgcaa aacctttcgc ggtatggcat      2760
gatagcgccc ggaagagagt caattcaggg tggtgaatgt gaaaccagta acgttatacg      2820
atgtcgcaga gtatgccggt gtctcttatc agaccgtttc ccgcgtggtg aaccaggcca      2880
gccacgtttc tgcgaaaacg cgggaaaaag tggaagcggc gatggcggag ctgaattaca      2940
ttcccaaccg cgtggcacaa caactggcgg gcaaacagtc gttgctgatt ggcgttgcca      3000
cctccagtct ggccctgcac gcgccgtcgc aaattgtcgc ggcgattaaa tctcgcgccg      3060
atcaactggg tgccagcgtg gtggtgtcga tggtagaacg aagcggcgtc gaagcctgta      3120
aagcggcggt gcacaatctt ctcgcgcaac gcgtcagtgg gctgatcatt aactatccgc      3180
tggatgacca ggatgccatt gctgtggaag ctgcctgcac taatgttccg gcgttatttc      3240
ttgatgtctc tgaccagaca cccatcaaca gtattatttt ctcccatgaa gacggtacgc      3300
gactgggcgt ggagcatctg gtcgcattgg gtcaccagca atcgcgctg ttagcgggcc       3360 cattaagttc tgtctcggcg cgtctgcgtc tggctggctg gcataaatat ctcactcgca      3420
atcaaattca gccgatagcg gaacgggaag gcgactggag tgccatgtcc ggttttcaac      3480
aaaccatgca aatgctgaat gagggcatcg ttcccactgc gatgctggtt gccaacgatc      3540
agatggcgct gggcgcaatg cgcgccatta ccgagtccgg gctgcgcgtt ggtgcggata      3600
tctcggtagt gggatacgac gataccgaag acagctcatg ttatatcccg ccgttaacca      3660
ccatcaaaca ggattttcgc ctgctggggc aaaccagcgt ggaccgcttg ctgcaactct      3720
ctcagggcca ggcggtgaag gcaatcagc tgttgcccgt ctcactggtg aaaagaaaaa       3780
ccaccctggc gcccaatacg caaaccgcct ctccccgcgc gttggccgat tcattaatgc      3840
agctggcacg acaggtttcc cgactggaaa gcgggcagtg agcgcaacgc aattaatgta      3900
agttagcgcg aattgatctg gtttgacagc ttatcatcga ctgcacggtg caccaatgct      3960
tctggcgtca gcagccatc ggaagctgtg gtatggctgt gcaggtcgta aatcactgca       4020
taattcgtgt cgctcaaggc gcactcccgt tctggataat gttttttgcg ccgacatcat      4080
aacggttctg gcaaatattc tgaaatgagc tgttgacaat taatcatccg gctcgtataa      4140
tgtgtggaat tgtgagcgga taacaatttc agaattcaaa gatctccac aattctagca       4200 tccacaacgg aggttccaaa tgcgccccct gcaccccatc gattttatct ttctgagcct      4260
```

-continued

```
ggaaaaacgc cagcagccca tgcacgtggg cggcctgttt ctgtttcaga tccccgataa    4320
cgccccgat  acctttatcc aggatctggt gaacgatatc cgcatcagca aaagcatccc    4380
cgtgccccc  tttaacaaca aactgaacgg cctgttttgg gatgaagatg aagaatttga    4440
tctggatcac cactttcgcc acatcgccct gccccacccc ggccgcatcc gcgaactgct    4500
gatctacatc agccaggaac acagcaccct gctggatcgc gccaaacccc tgtggacctg    4560
caacatcatc gaaggcatcg aaggcaaccg ctttgccatg tactttaaaa tccaccacgc    4620
catggtggat ggcgtggccg gcatgcgcct gatcgaaaaa agcctgagcc acgatgtgac    4680
cgaaaaaagc atcgtgcccc cctggtgcgt ggaaggcaaa cgcgccaaac gcctgcgcga    4740
acccaaaacc ggcaaaatca aaaaaatcat gagcggcatc aaaagccagc tgcaggccac    4800
ccccaccgtg atccaggaac tgagccagac cgtgttaaa  gatatcggcc gcaaccccga    4860
tcacgtgagc agctttcagg cccctgcag  catcctgaac cagcgcgtga gcagcagccg    4920
ccgctttgcc gcccagagct ttgatctgga tcgctttcgc aacatcgcca aaagcctgaa    4980
cgtgaccatc aacgatgtgg tgctggccgt gtgcagcggc gccctgcgcg cctacctgat    5040
gagccacaac agcctgccca gcaaacccct gatcgccatg gtgcccgcca gcatccgcaa    5100
cgatgatagc gatgtgagca accgcatcac catgatcctg ccaacctgg  ccacccacaa    5160
agatgatccc ctgcagcgcc tggaaatcat ccgccgcagc gtgcagaaca gcaaacagcg    5220
ctttaaacgc atgaccagcg atcagatcct gaactacagc gccgtggtgt acggccccgc    5280
cggcctgaac atcatcagcg gcatgatgcc caaacgccag gccttaacc  tggtgatcag    5340
caacgtgccc ggccccgcg  aaccctgta  ctggaacggc gccaaactgg atgccctgta    5400
ccccgccagc atcgtgctgg atggccaggc cctgaacatc accatgacca gctacctgga    5460
taaactggaa gtgggcctga tcgcctgccg caacgccctg ccccgcatgc agaacctgct    5520
gacccacctg gaagaagaaa tccagctgtt tgaaggcgtg atcgccaaac aggaagatat    5580
caaaaccgcc aactagggat ccaaactcga gtaaggatct ccaggcatca aataaaacga    5640
aaggctcagt cgaaagactg ggcctttcgt tttatctgtt gtttgtcggt gaacgctctc    5700
tactagagtc acactggctc accttcgggt gggcctttct gcgtttatac ctagggcgtt    5760
cggctgcggc gagcggtatc agctcactca aaggcggtaa tacgtccctg ctcgtcacgc    5820
tttcaggcac cgtgccagat atcgacgtgg agtcgatcac tgtgattggc gaaggggaag    5880
gcagcgctac ccaaatcgct agcttgctgg agaagctgaa acaaaccacg ggcattgatc    5940
tggcgaaatc cctaccgggt caatccgact cgcccgctgc gaagtcctaa gagatagcga    6000
tgtgaccgcg atcgcttgtc aagaatccca gtgatcccga accataggaa ggcaagctca    6060
atgcttgcct cgtcttgagg actatctaga tgtctgtgga acgcacattt attgccatca    6120
agcccgatgg cgttcagcgg ggtttggtcg gtacgatcat cggccgcttt gagcaaaaag    6180
gcttcaaact ggtgggccta aagcagctga agcccagtcg cgagctggcc gaacagcact    6240
atgctgtcca ccgcgagcgc cccttcttca atggcctcgt cgagttcatc acctctgggc    6300
cgatcgtggc gatcgtcttg gaaggcgaag gcgttgtggc ggctgctcgc aagttgatcg    6360
gcgctaccaa tccgctgacg gcagaaccgg gcaccatccg tggtgatttt ggtgtcaata    6420
ttggccgcaa catcatccat ggctcggatg caatcgaaac agcacaacag gaaattgctc    6480
tctggtttag cccagcagag ctaagtgatt ggaccccac  gattcaaccc tggctgtacg    6540
aataaggtct gcattccttc agagagacat tgccatgccg                          6580
```

<210> SEQ ID NO 8
<211> LENGTH: 6621
<212> TYPE: DNA
<213> ORGANISM: Artificial Sequence
<220> FEATURE:
<223> OTHER INFORMATION: pSe1Bb1s-Ws2 vector

<400> SEQUENCE: 8

```
gataatctca tgaccaaaat cccttaacgt gagttttcgt tccactgagc gtcagacccc      60
gtagaaaaga tcaaaggatc ttcttgagat cctttttttc tgcgcgtaat ctgctgcttg     120
caaacaaaaa aaccaccgct accagcggtg gtttgtttgc cggatcaaga gctaccaact     180
cttttttccga aggtaactgg cttcagcaga gcgcagatac caaatactgt tcttctagtg     240
tagccgtagt taggccacca cttcaagaac tctgtagcac cgcctacata cctcgctctg     300
ctaatcctgt taccagtggc tgctgccagt ggcgataagt cgtgtcttac cgggttggac     360
tcaagacgat agttaccgga taaggcgcag cggtcgggct gaacggggg ttcgtgcaca      420
cagcccagct tggagcgaac gacctacacc gaactgagat acctacagcg tgagctatga     480
gaaagcgcca cgcttcccga agggagaaag gcggacaggt atccggtaag cggcagggtc     540
ggaacaggag agcgcacgag ggagcttcca ggggggaaacg cctggtatct ttatagtcct     600
gtcgggtttc gccacctctg acttgagcgt cgatttttgt gatgctcgtc aggggggcgg     660
agcctatgga aaaacgccag caacgcggcc ttttacggtt cctggccttt tgctggcct     720
tttgctcaca tgtgtgctgg gccccaatgc cttctccaag ggcggcattc ccctgactgt     780
tgaaggcgtt gccaatatca agattgctgg ggaagaaccg accatccaca acgcgatcga     840
gcggctgctt ggcaaaaacc gtaaggaaat cgagcaaatt gccaaggaga ccctcgaagg     900
caacttgcgt ggtgttttag ccagcctcac gccggagcag atcaacgagg acaaaattgc     960
ctttgccaaa agtctgctgg aagaggcgga ggatgacctt gagcagctgg gtcaagtcct    1020
cgatacgctg caagtccaga acatttccga tgaggtcggt tatctctcgg ctagtggacg    1080
caagcagcgg gctgatctgc agcgagatgc ccgaattgct gaagccgatg cccaggctgc    1140
ctctgcgatc caaacggccg aaaatgacaa gatcacggcc ctgcgtcgga tcgatcgcga    1200
tgtagcgatc gcccaagccg aggccgagcg ccggattcag gatgcgttga gcggcgcga    1260
agcggtggtg gccgaagctg aagcggacat tgctaccgaa gtcgctcgta gccaagcaga    1320
actccctgtg cagcaggagc ggatcaaaca ggtgcagcag caacttcaag ccgatgtgat    1380
cgccccagct gaggcagctt gtaaacgggc gatcgcggaa gcgcgggggg ccgccgcccg    1440
tatcgtcgaa gatggaaaag ctcaagcgga agggacccaa cggctggcgg aggcttggca    1500
gaccgctggt gctaatgccc gcgacatctt cctgctccag aagtctagac cagccaggac    1560
agaaatgcct cgacttcgct gctacccaag gttgccgggt gacgcacacc gtggaaacgg    1620
atgaaggcac gaacccagtg gacataagcc tgttcggttc gtaagctgta atgcaagtag    1680
cgtatgcgct cacgcaactg gtccagaacc ttgaccgaac gcagcggtgg taacggcgca    1740
gtggcggttt tcatggcttg ttatgactgt tttttggggt acagtctat gcctcgggca    1800
tccaagcagc aagcgcgtta cgccgtgggt cgatgtttga tgttatggag cagcaacgat    1860
gttacgcagc agggcagtcg ccctaaaaca agttaaaca ttatgaggga agcggtgatc      1920
gccgaagtat cgactcaact atcagaggta gttggcgtca tcgagcgcca tctcgaaccg    1980
acgttgctgg ccgtacattt gtacggctcc gcagtggatg cgggcctgaa gccacacagt    2040
gatattgatt tgctggttac ggtgaccgta aggcttgatg aaacaacgcg gcgagctttg    2100
```

```
atcaacgacc ttttggaaac ttcggcttcc cctggagaga gcgagattct ccgcgctgta      2160
gaagtcacca ttgttgtgca cgacgacatc attccgtggc gttatccagc taagcgcgaa      2220
ctgcaatttg gagaatggca gcgcaatgac attcttgctg gtatcttcga gccagccacg      2280
atcgacattg atctggctat cttgctgaca aaagcaagag aacatagcgt tgccttggta      2340
ggtccagcgg cggaggaact ctttgatccg gttcctgaac aggatctatt tgaggcgcta      2400
aatgaaacct taacgctatg gaactcgccg cccgactggg ctggcgatga gcgaaatgta      2460
gtgcttacgt tgtcccgcat ttggtacagc gcagtaaccg gcaaaatcgc gccgaaggat      2520
gtcgctgccg actgggcaat ggagcgcctg ccggcccagt atcagcccgt catacttgaa      2580
gctagacagg cttatcttgg acaagaagaa gatcgcttgg cctcgcgcgc agatcagttg      2640
gaagaatttg tccactacgt gaaaggcgag atcaccaagg tagtcggcaa ataacctcat      2700
tttcgccaga tatcgacgtc gacaccatcg aatggtgcaa aacctttcgc ggtatggcat      2760
gatagcgccc ggaagagagt caattcaggg tggtgaatgt gaaaccagta acgttatacg      2820
atgtcgcaga gtatgccggt gtctcttatc agaccgtttc cgcgtggtg aaccaggcca      2880 gccacgtttc tgcgaaaacg cgggaaaaag tggaagcggc gatggcggag ctgaattaca      2940
ttcccaaccg cgtggcacaa caactggcgg gcaaacagtc gttgctgatt ggcgttgcca      3000
cctccagtct ggccctgcac gcgccgtcgc aaattgtcgc ggcgattaaa tctcgcgccg      3060
atcaactggg tgccagcgtg gtggtgtcga tggtagaacg aagcggcgtc gaagcctgta      3120
aagcggcggt gcacaatctt ctcgcgcaac gcgtcagtgg gctgatcatt aactatccgc      3180
tggatgacca ggatgccatt gctgtggaag ctgcctgcac taatgttccg gcgttatttc      3240
ttgatgtctc tgaccagaca cccatcaaca gtattatttt ctcccatgaa gacggtacgc      3300
gactgggcgt ggagcatctg gtcgcattgg gtcaccagca atcgcgctg ttagcgggcc      3360 cattaagttc tgtctcggcg cgtctgcgtc tggctggctg cataaatat ctcactcgca      3420 atcaaattca gccgatagcg gaacgggaag gcgactggag tgccatgtcc ggttttcaac      3480
aaaccatgca aatgctgaat gagggcatcg ttcccactgc gatgctggtt gccaacgatc      3540
agatggcgct gggcgcaatg cgcgccatta ccgagtccgg gctgcgcgtt ggtgcggata      3600
tctcggtagt gggatacgac gataccgaag acagctcatg ttatatcccg ccgttaacca      3660
ccatcaaaca ggattttcgc ctgctggggc aaaccagcgt ggaccgcttg ctgcaactct      3720
ctcagggcca ggcggtgaag ggcaatcagc tgttgcccgt ctcactggtg aaaagaaaaa      3780
ccaccctggc gcccaatacg caaaccgcct ctccccgcgc gttggccgat tcattaatgc      3840
agctggcacg acaggtttcc cgactggaaa gcgggcagtg agcgcaacgc aattaatgta      3900
agttagcgcg aattgatctg gtttgacagc ttatcatcga ctgcacggtg caccaatgct      3960
tctggcgtca ggcagccatc ggaagctgtg gtatggctgt gcaggtcgta atcactgca      4020 taattcgtgt cgctcaaggc gcactcccgt tctggataat gttttttgcg ccgacatcat      4080
aacggttctg gcaaatattc tgaaatgagc tgttgacaat taatcatccg gctcgtataa      4140
tgtgtggaat tgtgagcgga taacaatttc agaattcaaa agatctgtta ccataagtca      4200
agaaggaggt attaaatgaa acgcctgggc accctgggatg ccagctggct ggccgtggaa      4260
agcgaagata cccccatgca cgtgggcacc ctgcagattt ttagcctgcc cgaaggcgcc      4320
cccgaaacct ttctgcgcga tatggtgacc cgcatgaaag aagccggcga tgtggccccc      4380 ccctgggct acaaactggc ctggagcggc tttctgggcc gcgtgatcgc cccgcctgg      4440 aaagtggata agatatcga tctggattac cacgtgcgcc acagcgccct gccccgcccc      4500
```

```
ggcggcgaac gcgaactggg catcctggtg agccgcctgc acagcaaccc cctggatttt   4560
agccgccccc tgtgggaatg ccacgtgatc gaaggcctgg aaaacaaccg ctttgccctg   4620
tacaccaaaa tgcaccacag catgatcgat ggcatcagcg gcgtgcgcct gatgcagcgc   4680
gtgctgacca ccgatcccga acgctgcaac atgcccccc cctggaccgt gcgccccac    4740 cagcgccgcg cgccaaaac cgataaagaa gccagcgtgc ccgccgccgt gagccaggcc   4800
atggatgccc tgaaactgca ggccgatatg gcccccccgcc tgtggcaggc cggcaaccgc  4860
ctggtgcaca gcgtgcgcca ccccgaagat ggcctgaccg cccccttac cggccccgtg   4920 agcgtgctga accaccgcgt gaccgcccag cgccgctttg ccacccagca ctaccagctg   4980
gatcgcctga aaacctggcc ccacgccagc ggcggcagcc tgaacgatat cgtgctgtac   5040
ctgtgcggca ccgccctgcg ccgctttctg gccgaacaga caacctgccc cgatacccccc  5100 ctgaccgccg gcatccccgt gaacatccgc cccgccgatg atgaaggcac cggcacccag   5160
atcagcttta tgatcgccag cctggccacc gatgaagccg atcccctgaa ccgcctgcag   5220
cagatcaaaa ccagcacccg ccgcgccaaa gaacaccctg agaaactgcc caaaagcgcc   5280
ctgacccagt acaccatgct gctgatgagc ccctacatcc tgcagctgat gagcggcctg   5340
ggcggccgca tgcgccccgt gtttaacgtg accatcagca acgtgcccgg ccccgaaggc   5400
accctgtact acgaaggcgc ccgcctggaa gccatgtacc ccgtgagcct gatcgcccac   5460
ggcggcgccc tgaacatcac ctgcctgagc tacgccggca gctgaacttt ggctttacc    5520 ggctgccgcg ataccctgcc cagcatgcag aaactggccg tgtacaccgg cgaagccctg   5580
gatgaactgg aaagcctgat cctgcccccc aaaaaacgcg cccgcacccg caaatagcga   5640
tccaaactcg agtaaggatc tccaggcatc aaataaaacg aaaggctcag tcgaaagact   5700
gggcctttcg ttttatctgt tgtttgtcgg tgaacgctct ctactagagt cacactggct   5760
caccttcggg tgggcctttc tgcgtttata cctagggcgt tcggctgcgg cgagcggtat   5820
cagctcactc aaaggcggta atacgtccct gctcgtcacg ctttcaggca ccgtgccaga   5880
tatcgacgtg gagtcgatca ctgtgattgg cgaaggggaa ggcagcgcta cccaaatcgc   5940
tagcttgctg gagaagctga acaaaaccac gggcattgat ctggcgaaat ccctaccggg   6000
tcaatccgac tcgcccgctg cgaagtccta agagatagcg atgtgaccgc gatcgcttgt   6060
caagaatccc agtgatcccg aaccatagga aggcaagctc aatgcttgcc tcgtcttgag   6120
gactatctag atgtctgtgg aacgcacatt tattgccatc aagcccgatg gcgttcagcg   6180
gggtttggtc ggtacgatca tcggccgctt tgagcaaaaa ggcttcaaac tggtgggcct   6240
aaagcagctg aagcccagtc gcgagctggc cgaacagcac tatgctgtcc accgcgagcg   6300 cccccttcttc aatggcctcg tcgagttcat cacctctggg ccgatcgtgg cgatcgtctt   6360
ggaaggcgaa ggcgttgtgg cggctgctcg caagttgatc ggcgctacca atccgctgac   6420
ggcagaaccg gcaccatccc gtggtgattt tggtgtcaat attggccgca acatcatcca   6480
tggctcggat gcaatcgaaa cagcacaaca ggaaattgct ctctggttta gcccagcaga   6540
gctaagtgat tggaccccca cgattcaacc ctggctgtac gaataaggtc tgcattcctt   6600
cagagagaca ttgccatgcc g                                            6621
```

<210> SEQ ID NO 9
<211> LENGTH: 6621
<212> TYPE: DNA
<213> ORGANISM: Artificial Sequence
<220> FEATURE:
<223> OTHER INFORMATION: pSe[FadE]Bb1c-tesA vector

<400> SEQUENCE: 9

```
gataatctca tgaccaaaat cccttaacgt gagttttcgt tccactgagc gtcagacccc    60
gtagaaaaga tcaaaggatc ttcttgagat cctttttttc tgcgcgtaat ctgctgcttg   120
caaacaaaaa aaccaccgct accagcggtg gtttgtttgc cggatcaaga gctaccaact   180
cttttttccga aggtaactgg cttcagcaga gcgcagatac caaatactgt tcttctagtg   240
tagccgtagt taggccacca cttcaagaac tctgtagcac cgcctacata cctcgctctg   300
ctaatcctgt taccagtggc tgctgccagt ggcgataagt cgtgtcttac cgggttggac   360
tcaagacgat agttaccgga taaggcgcag cggtcgggct gaacggggggg ttcgtgcaca   420
cagcccagct tggagcgaac gacctacacc gaactgagat acctacagcg tgagctatga   480
gaaagcgcca cgcttcccga agggagaaag gcggacaggt atccggtaag cggcagggtc   540
ggaacaggag agcgcacgag ggagcttcca gggggaaacg cctggtatct ttatagtcct   600
gtcgggtttc gccacctctg acttgagcgt cgattttgt gatgctcgtc aggggggcgg   660
agcctatgga aaaacgccag caacgcggcc ttttttacgg ttcctggcctt ttgctggcct   720
tttgctcaca tgtgtgctgg ccccaatgc cttctccaag gcggcattc ccctgactgt   780
tgaaggcgtt gccaatatca agattgctgg ggaagaaccg accatccaca acgcgatcga   840
gcggctgctt ggcaaaaacc gtaaggaaat cgagcaaatt gccaaggaga ccctcgaagg   900
caacttgcgt ggtgttttag ccagcctcac gccggagcag atcaacgagg acaaaattgc   960
ctttgccaaa agtctgctgg aagaggcgga ggatgacctt gagcagctgg gtcaagtcct  1020
cgatacgctg caagtccaga acatttccga tgaggtcggt tatctctcgg ctagtggacg  1080
caagcagcgg gctgatctgc agcgagatgc ccgaattgct gaagccgatg cccaggctgc  1140
ctctgcgatc caaacggccg aaaatgacaa gatcacggcc ctgcgtcgga tcgatcgcga  1200
tgtagcgatc gcccaagccg aggccgagcg ccggattcag gatgcgttga cgcggcgcga  1260
agcggtggtg gccgaagctg aagcggacat tgctaccgaa gtcgctcgta gccaagcaga  1320
actccctgtg cagcaggagc ggatcaaaca ggtgcagcag caacttcaag ccgatgtgat  1380
cgccccagct gaggcagctt gtaaacgggc gatcgcggaa gcgcgggggg ccgccgcccg  1440
tatcgtcgaa gatggaaaag ctcaagcgga agggacccaa cggctggcgg aggcttggca  1500
gaccgctggt gctaatgccc gcgacatctt cctgctccag aagtctagac cagccaggac  1560
agaaatgcct cgacttcgct gctacccaag gttgccgggt gacgcacacc gtggaaacgg  1620
atgaaggcac gaacccagtg gacataagcc tgttcggttc gtaagctgta atgcaagtag  1680
cgtatgcgct cacgcaactg gtccagaacc ttgaccgaac gcagcggtgg taacggcgca  1740
gtggcggttt tcatggcttg ttatgactgt ttttttgggg tacagtctat gcctcgggca  1800
tccaagcagc aagcgcgtta cgccgtgggt cgatgtttga tgttatggag cagcaacgat  1860
gttacgcagc agggcagtcg ccctaaaaca aagttaaaca ttatgaggga agcggtgatc  1920
gccgaagtat cgactcaact atcagaggta gttggcgtca tcgagcgcca tctcgaaccg  1980
acgttgctgg ccgtacattt gtacggctcc gcagtggatg gcggcctgaa gccacacagt  2040
gatattgatt tgctggttac ggtgaccgta aggcttgatg aaacaacgcg gcgagctttg  2100
atcaacgacc ttttggaaac ttcggcttcc cctggagaga gcgagattct ccgcgctgta  2160
gaagtcacca ttgttgtgca cgacgacatc attccgtggc gttatccagc taagcgcgaa  2220
ctgcaatttg gagaatggca gcgcaatgac attcttgctg gtatcttcga gccagccacg  2280
atcgacattg atctggctat cttgctgaca aaagcaagag aacatagcgt tgccttggta  2340
```

```
ggtccagcgg cggaggaact ctttgatccg gttcctgaac aggatctatt tgaggcgcta    2400
aatgaaacct taacgctatg gaactcgccg cccgactggg ctggcgatga gcgaaatgta    2460
gtgcttacgt tgtcccgcat ttggtacagc gcagtaaccg gcaaaatcgc gccgaaggat    2520
gtcgctgccg actgggcaat ggagcgcctg ccggcccagt atcagcccgt catacttgaa    2580
gctagacagg cttatcttgg acaagaagaa gatcgcttgg cctcgcgcgc agatcagttg    2640
gaagaatttg tccactacgt gaaaggcgag atcaccaagg tagtcggcaa ataacctcat    2700
tttcgccaga tatcgacgtc gacaccatcg aatggtgcaa aaccttttcgc ggtatggcat    2760 gatagcgccc ggaagagagt caattcaggg tggtgaatgt gaaaccagta acgttatacg    2820
atgtcgcaga gtatgccggt gtctcttatc agaccgtttc ccgcgtggtg aaccaggcca    2880
gccacgtttc tgcgaaaacg cgggaaaaag tggaagcggc gatggcggag ctgaattaca    2940
ttcccaaccg cgtggcacaa caactggcgg gcaaacagtc gttgctgatt ggcgttgcca    3000
cctccagtct ggccctgcac gcgccgtcgc aaattgtcgc ggcgattaaa tctcgcgccg    3060
atcaactggg tgccagcgtg gtggtgtcga tggtagaacg aagcggcgtc gaagcctgta    3120
aagcggcggt gcacaatctt ctcgcgcaac gcgtcagtgg gctgatcatt aactatccgc    3180
tggatgacca ggatgccatt gctgtggaag ctgcctgcac taatgttccg gcgttatttc    3240
ttgatgtctc tgaccagaca cccatcaaca gtattatttt ctcccatgaa gacggtacgc    3300
gactgggcgt ggagcatctg gtcgcattgg gtcaccagca aatcgcgctg ttagcgggcc    3360
cattaagttc tgtctcggcg cgtctgcgtc tggctggctg gcataaatat ctcactcgca    3420
atcaaattca gccgatagcg gaacgggaag gcgactggaa tgccatgtcc ggttttcaac    3480
aaaccatgca aatgctgaat gagggcatcg ttcccactgc gatgctggtt gccaacgatc    3540
agatggcgct gggcgcaatg cgcgccatta ccgagtccgg gctgcgcgtt ggtgcggata    3600
tctcggtagt gggatacgac gataccgaag acagctcatg ttatatcccg ccgttaacca    3660
ccatcaaaca ggattttcgc ctgctggggc aaaccagcgt ggaccgcttg ctgcaactct    3720
ctcagggcca ggcggtgaag ggcaatcagc tgttgcccgt ctcactggtg aaaagaaaaa    3780
ccaccctggc gcccaatacg caaaccgcct ctccccgcgc gttggccgat tcattaatgc    3840
agctggcacg acaggtttcc cgactggaaa gcgggcagtg agcgcaacgc aattaatgta    3900
agttagcgcg aattgatctg gtttgacagc ttatcatcga ctgcacggtg caccaatgct    3960
tctggcgtca ggcagccatc ggaagctgtg gtatggctgt gcaggtcgta aatcactgca    4020
taattcgtgt cgctcaaggc gcactcccgt tctggataat gttttttgcg ccgacatcat    4080
aacggttctg gcaaatattc tgaaatgagc tgttgacaat taatcatccg gctcgtataa    4140
tgtgtggaat tgtgagcgga taacaatttc agaattcaaa agatctgtta ccataagtca    4200
agaaggaggt attaaatgaa acgcctgggc accctggatg ccagctggct ggccgtggaa    4260
agcgaagata ccccccatgca cgtgggcacc ctgcagattt ttagcctgcc cgaaggcgcc    4320
cccgaaacct ttctgcgcga tatggtgacc cgcatgaaag aagccggcga tgtggccccc    4380
ccctggggct acaaactggc ctggagcggc tttctgggcc gcgtgatcgc cccgcctgg    4440 aaagtggata agatatcga tctggattac cacgtgcgcc acagcgccct gccccgcccc    4500
ggcggcgaac gcgaactggg catcctggtg agccgcctgc acagcaaccc cctggatttt    4560
agccgccccc tgtgggaatg ccacgtgatc gaaggcctgg aaaacaaccg ctttgccctg    4620
tacaccaaaa tgcaccacag catgatcgat ggcatcagcg gcgtgcgcct gatgcagcgc    4680
gtgctgacca ccgatcccga acgctgcaac atgccccccc cctggaccgt gcgccccac    4740
```

```
cagcgccgcg gcgccaaaac cgataaagaa gccagcgtgc ccgccgccgt gagccaggcc    4800
atggatgccc tgaaactgca ggccgatatg gcccccgcc  tgtggcaggc cggcaaccgc    4860
ctggtgcaca gcgtgcgcca ccccgaagat ggcctgaccg ccccctttac cggccccgtg    4920
agcgtgctga accaccgcgt gaccgcccag cgccgctttg ccacccagca ctaccagctg    4980
gatcgcctga aaacctggcc ccacgccagc ggcggcagcc tgaacgatat cgtgctgtac    5040
ctgtgcggca ccgccctgcg ccgctttctg gccgaacaga acaacctgcc cgatacccc     5100 ctgaccgccg gcatccccgt gaacatccgc cccgccgatg atgaaggcac cggcacccag    5160
atcagcttta tgatcgccag cctggccacc gatgaagccg atccctgaa  ccgcctgcag    5220 cagatcaaaa ccagcacccg ccgcgccaaa gaacacctgc agaaactgcc caaaagcgcc    5280
ctgacccagt acaccatgct gctgatgagc ccctacatcc tgcagctgat gagcggcctg    5340
ggcggccgca tgcgccccgt gtttaacgtg accatcagca acgtgcccgg ccccgaaggc    5400
accctgtact acgaaggcgc ccgcctggaa gccatgtacc ccgtgagcct gatcgcccac    5460
ggcggcgccc tgaacatcac ctgcctgagc tacgccggca gcctgaactt tggctttacc    5520
ggctgccgcg ataccctgcc cagcatgcag aaactggccg tgtacaccgg cgaagccctg    5580
gatgaactgg aaagcctgat cctgcccccc aaaaaacgcg cccgcacccg caaatagcga    5640
tccaaactcg agtaaggatc tccaggcatc aaataaaacg aaaggctcag tcgaaagact    5700
gggcctttcg ttttatctgt tgtttgtcgg tgaacgctct ctactagagt cacactggct    5760
caccttcggg tgggcctttc tgcgtttata cctagggcgt tcggctgcgg cgagcggtat    5820
cagctcactc aaaggcggta atacgtccct gctcgtcacg ctttcaggca ccgtgccaga    5880
tatcgacgtg gagtcgatca ctgtgattgg cgaagggaa  ggcagcgcta cccaaatcgc    5940
tagcttgctg gagaagctga acaaaccac  gggcattgat ctggcgaaat ccctaccggg    6000
tcaatccgac tcgcccgctg cgaagtccta agagatagcg atgtgaccgc gatcgcttgt    6060
caagaatccc agtgatcccg aaccatagga aggcaagctc aatgcttgcc tcgtcttgag    6120
gactatctag atgtctgtgg aacgcacatt tattgccatc aagcccgatg gcgttcagcg    6180
gggtttggtc ggtacgatca tcggccgctt tgagcaaaaa ggcttcaaac tggtgggcct    6240
aaagcagctg aagcccagtc gcgagctggc cgaacagcac tatgctgtcc accgcgagcg    6300
ccccttcttc aatggcctcg tcgagttcat cacctctggg ccgatcgtgg cgatcgtctt    6360
ggaaggcgaa ggcgttgtgg cggctgctcg caagttgatc ggcgctacca atccgctgac    6420
ggcagaaccg ggcaccatcc gtggtgattt tggtgtcaat attggccgca acatcatcca    6480
tggctcggat gcaatcgaaa cagcacaaca ggaaattgct ctctggttta gcccagcaga    6540
gctaagtgat tggacccca  cgattcaacc ctggctgtac gaataaggtc tgcattcctt    6600
cagagagaca ttgccatgcc g                                              6621
```

TRANSFORMED *SYNECHOCOCCUS ELONGATUS* HAVING CAPABILITY OF PRODUCING BIODIESEL FROM CARBON DIOXIDE AND METHOD FOR PRODUCING BIODIESEL USING THE SAME

CROSS-REFERENCE TO RELATED APPLICATION

This application claims priority to Korean Patent Application No. 10-2015-0147216, filed on Oct. 22, 2015, and all the benefits accruing therefrom under 35 U.S.C. § 119, the contents of which in its entirety are herein incorporated by reference.

DESCRIPTION ABOUT NATIONAL SUPPORT RESEARCH AND DEVELOPMENT

This study is made by the support of Development of Technique for Climate Change Response Business of the Korean Ministry of Science, ICT and Future Planning under the supervision of the Korea Institute of Science and Technology, and the subject name thereof is Development of original technology of using recombinant cyanobacteria for continuous direct production of biodiesel (2N38970) (Subject Identification No.: 2014049277).

BACKGROUND

1. Field

The present disclosure relates to a transformed *Synechococcus elongatus* strain capable of producing biodiesel directly from carbon dioxide and a method for producing biodiesel and a method for removing carbon dioxide using the same.

2. Description of the Related Art

With the crisis of depletion of limited energy resources due to the mass consumption of fossil fuels, oil prices remain high consistently and the problems of global warming and environmental pollution persist. For this reason, researches are actively ongoing worldwide on various types of energy sources that can replace fossil fuels. Many researches and efforts are being made also in Korea, which is heavily dependent on imports of energy resources. Until now, the development of bioenergy as a renewable alternative energy source has been quite successful. In particular, biodiesel which can be produced from recyclable animal or plant oil is drawing attentions as a clean alternative fuel.

Biodiesel is mostly produced from vegetable oils such as soybean oil, palm oil, etc. However, Korea relies mainly on imported soybean oil or palm oil, as the raw materials of biodiesel, and their prices are high and unstable because they are food-related resources greatly affected by the change in international environment. In this situation, Korea's energy security is threatened not only be petroleum but also by alternative fuels and, therefore, it is urgently needed to provide measures to utilize inexpensive raw materials or domestic resources.

SUMMARY

In an aspect, the present disclosure is directed to providing a *Synechococcus elongatus* strain having capability of producing biodiesel.

In another aspect, the present disclosure is directed to producing biodiesel by an environment-friendly method using microorganisms.

In another aspect, the present disclosure is directed to producing biodiesel in large scale using the *Synechococcus elongatus* strain.

In another aspect, the present disclosure is directed to producing biodiesel while removing carbon dioxide in the atmosphere.

In an aspect, the present disclosure provides a *Synechococcus elongatus* strain containing: a gene encoding an enzyme which produces acetaldehyde from pyruvate; a gene encoding an enzyme which produces ethanol from acetaldehyde; and gene encoding an enzyme which produces biodiesel from acyl-coenzyme A and ethanol.

In another aspect, the present disclosure provides a method for producing biodiesel, which includes a step of culturing the *Synechococcus elongatus* strain.

In another aspect, the present disclosure provides a method for removing carbon dioxide, which includes a step of culturing the *Synechococcus elongatus* strain.

In an aspect, the transformed *Synechococcus elongatus* strain of the present disclosure can produce biodiesel in large scale using carbon dioxide as a carbon source. The *Synechococcus elongatus* strain can economically produce biodiesel using carbon dioxide present in the atmosphere as a carbon source and the produced biodiesel is excreted extracellularly and can be used conveniently without an additional process. In addition, the present disclosure is environment-friendly because it can be used to remove or reduce carbon dioxide in the atmosphere using the microorganism. The strain of the present disclosure is advantageous in that it can produce biodiesel in large scale because it grows faster and exhibits excellent carbon dioxide fixation capability as compared to other photosynthetic microorganisms.

DETAILED DESCRIPTION

Figure 1:
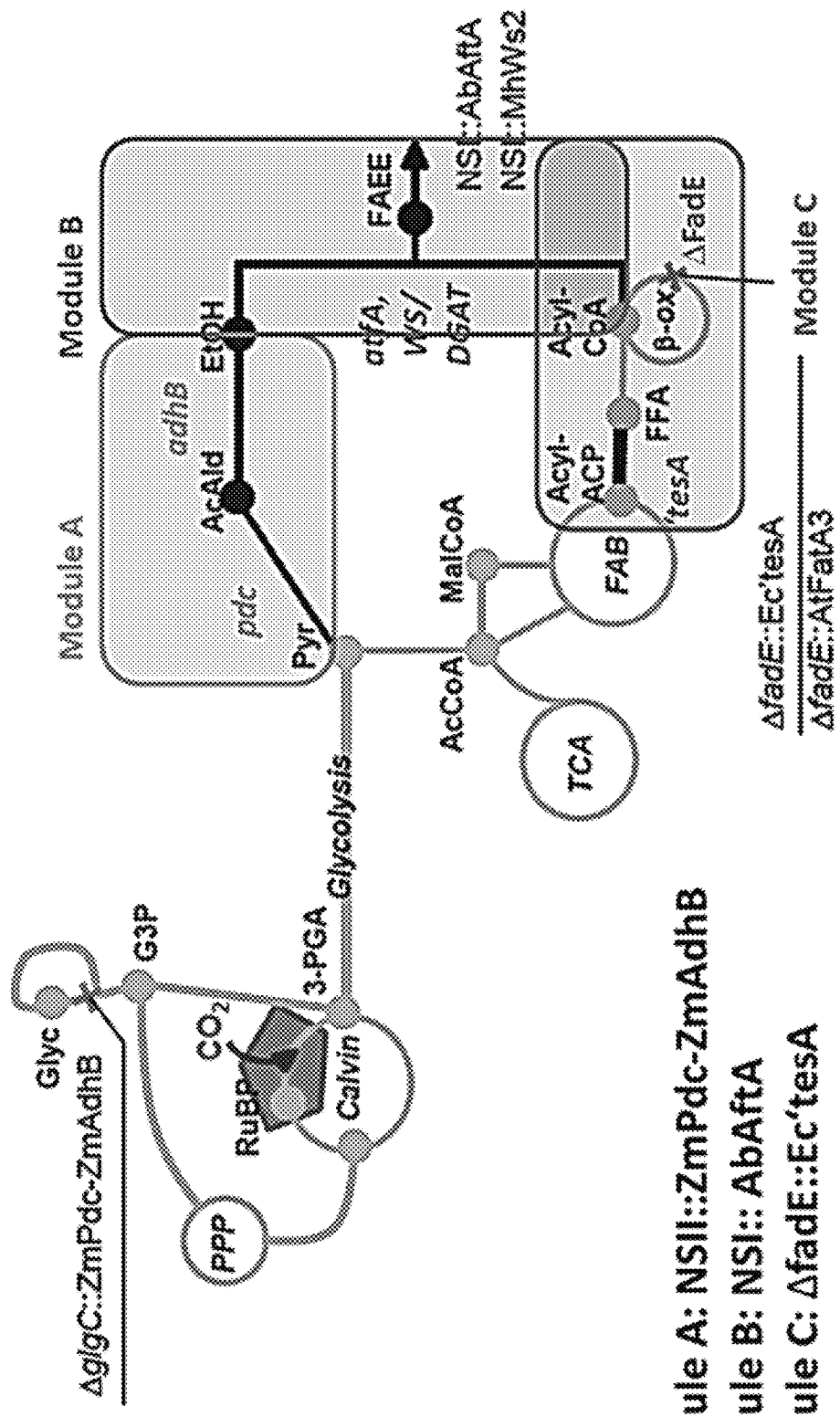
FIG. 1 schematically shows the fatty acid ethyl ester (FAEE) production pathway of a transformed *Synechococcus elongatus* strain.

Hereinafter, the present disclosure is described in detail.

Synechococcus elongatus is a species of cyanobacteria. The prokaryotic cyanobacteria are useful in changing metabolic pathways or controlling metabolites artificially because genetic manipulation is easy. The inventors of the present disclosure have completed the present disclosure by utilizing these characteristics of cyanobacteria and synthetic biological/metabolic engineering techniques.

In an aspect, the present disclosure provides a Synechococcus elongatus strain containing: a gene encoding an enzyme which produces acetaldehyde from pyruvate; a gene encoding an enzyme which produces ethanol from acetaldehyde; and gene encoding an enzyme which produces biodiesel from acyl-coenzyme A and ethanol.

In the present disclosure, biodiesel may refer to an ester converted from a triglyceride, which is the main component of plant oil or animal fat, through reaction with an alcohol. For example, one glycerin molecule and three biodiesel molecules may be produced from the reaction of one triglyceride molecule and three alcohol molecules in the presence of a catalyst. For another example, biodiesel can be produced from the reaction of ethanol with acyl-coenzyme A.

In an exemplary embodiment, the strain may further contain a gene encoding an enzyme which produces a free fatty acid from an acyl-acyl carrier protein (acyl-ACP). The produced free fatty acid may be used to produce biodiesel.

In this aspect, the enzyme which produces acetaldehyde from pyruvate may be pyruvate decarboxylase, the enzyme which produces ethanol from acetaldehyde may be alcohol dehydrogenase and the enzyme which produces biodiesel from acyl-coenzyme A and ethanol may be wax-ester synthase.

And, the enzyme which produces a free fatty acid from an acyl-acyl carrier protein (acyl-ACP) may be thioesterase.

In the present disclosure, a module may refer to a functional unit having a particular function, such as a set of genes capable of expressing a particular gene. In the present disclosure, a module having capability of producing ethanol from pyruvate is referred to as a module A, a module having capability of producing a free fatty acid and acyl-coenzyme A from an acyl-acyl carrier protein is referred to as a module C and a module having capability of producing biodiesel from ethanol and acyl-coenzyme A is referred to as a module B. Accordingly, a gene encoding an enzyme which produces acetaldehyde from pyruvate and a gene encoding an enzyme which produces ethanol from acetaldehyde may be called genes constituting the module A, a gene encoding an enzyme which produces a free fatty acid from an acyl-acyl carrier protein (acyl-ACP) may be called a gene constituting the module C, and a gene encoding an enzyme which produces biodiesel from acyl-coenzyme A and ethanol may be called a gene constituting the module B.

In this aspect, a gene encoding pyruvate decarboxylase may contain a sequence of SEQ ID NO: 1, a gene encoding alcohol dehydrogenase may contain a sequence of SEQ ID NO: 2, and a gene encoding wax-ester synthase may contain a sequence of SEQ ID NO: 3 or SEQ ID NO: 4. And, a gene encoding thioesterase may contain a sequence of SEQ ID NO: 5.

For example, the gene encoding pyruvate decarboxylase may be derived from a pdc gene of *Zymomonas mobilis*, the gene encoding alcohol dehydrogenase may be derived from an adh gene of *Zymomonas mobilis*, and the gene encoding wax-ester synthase may be derived from an atfA gene of *Acinetobacter* sp. or a Ws2 gene of *Marinobacter hydrocarbonoclasticus* ATCC49840. These genes may be obtained by consulting the following literature: Microbial production of fatty-acid-derived fuels and chemicals from plant biomass (2010). *Nature*, 463(7280), 559-562. Steen, E. J., Kang, Y., Bokinsky, G., Hu, Z., Schirmer, A., McClure, A., Del Cardayre SB & Keasling, J. D.

And, the gene encoding thioesterase may be derived from a tesA gene of *E. coli*.

pdc is a gene encoding pyruvate decarboxylase of *Zymomonas mobilis* strain, adh is a gene encoding alcohol dehydrogenase of *Zymomonas mobilis* strain, atfA of *Acinetobacter* sp. and Ws2 of *Marinobacter hydrocarbonoclasticus* ATCC 49840 are genes encoding wax-ester synthase, and tesA is a gene encoding thioesterase of *E. coli*.

In an exemplary embodiment, the sequence derived from pdc may be a sequence of SEQ ID NO: 1, the sequence derived from adh may be a sequence of SEQ ID NO: 2, the sequence derived from atfA may be a sequence of SEQ ID NO: 3, the sequence derived from Ws2 may be a sequence of SEQ ID NO: 4, and the sequence derived from tesA may be a sequence of SEQ ID NO: 5.

These genes are codon-optimized for stable expression in the parent strain *Synechococcus elongatus*.

In an exemplary embodiment, the strain may be a *Synechococcus elongatus* strain transformed with a first vector containing a sequence derived from the pdc gene of *Zymomonas mobilis* and a sequence derived from the adh gene of *Zymomonas mobilis* and a second vector containing a sequence derived from the atfA gene of *Acinetobacter* or a sequence derived from the Ws2 gene of *Marinobacter hydrocarbonoclasticus*. For example, the first vector may be represented by a pSe2Bb1k-pdc,adh vector (SEQ ID NO: 6) and the second vector may be represented by a pSe1Bb1s-atfA vector (SEQ ID NO: 7) or a pSe1Bb1s-Ws2 vector (SEQ ID NO: 8).

The sequence listing submitted together with the present disclosure is incorporated herein in its entirety.

In another exemplary embodiment, the strain may be a *Synechococcus elongatus* strain transformed with the first vector and the second vector and further transformed with a third vector containing a sequence derived from the tesA gene of *E. coli*. The third vector may be represented by a pSe[FadE]Bb1c-tesA vector (SEQ ID NO: 9).

In all the vectors disclosed in the present disclosure, the genes are linked operably. "Operable" means that the target gene can be expressed normally.

In this aspect, the strain may be a transformed *Synechococcus elongatus* strain wherein the first vector is inserted at the neutral site II (NSII) of the parent strain *Synechococcus elongatus* and the second vector is inserted at the neutral site I (NSI) of the parent strain *Synechococcus elongatus*. Also, in this aspect, the third vector may be inserted at the FadE site of the parent strain *Synechococcus elongatus*.

In this aspect, the first vector may contain, in sequence, a kanamycin resistance gene, a lacI repressor, a trc promoter, the gene encoding pyruvate decarboxylase and the gene encoding alcohol dehydrogenase.

Also, the second vector may contain, in sequence, a spectinomycin resistance gene, a lacI repressor, a trc promoter and the gene encoding wax-ester synthase.

Also, the third vector may contain, in sequence, a chloramphenicol resistance gene, a lacI repressor, a trc promoter and the gene encoding thioesterase. The genes contained in the vectors are the same as described above.

In an aspect, the first vector may contain a sequence of SEQ ID NO: 6 and the second vector may contain a sequence of SEQ ID NO: 7 or SEQ ID NO: 8. And, the third vector may contain a sequence of SEQ ID NO: 9.

In an exemplary embodiment, the strain transformed with the vectors is derived from the parent strain *Synechococcus elongatus* PCC7942 (ATCC 33912).

In an aspect of the present disclosure, the biodiesel may be a fatty acid ethyl ester (FAEE), although not being limited thereto. In particular, the fatty acid ethyl ester may be hexadecanoic acid ethyl ester or octadecanoic acid ethyl ester, although not being limited thereto.

In an exemplary embodiment, the strain of the present disclosure may be a *Synechococcus elongatus* strain with an accession number KCTC 12883BP or an accession number KCTC 12884BP.

The strain with an accession number KCTC 12883BP may be a strain transformed the pSe2Bb1k-pdc,adh vector and the strain with an accession number KCTC 12884BP strain may be a strain transformed the pSe2Bb1k-pdc,adh vector, the pSe1Bb1s-atfA vector and the pSe[FadE]Bb1c-tesA vector.

The strain of the present disclosure may absorb and fix carbon dioxide.

In another aspect, the present disclosure provides a method for producing biodiesel, which includes a step of culturing the *Synechococcus elongatus* strain.

In this aspect, the step of culturing the strain may include supplying carbon dioxide.

In this aspect, the method may further include a step of separating and obtaining the biodiesel dissolved in a hydrophobic solvent. Any known hydrophobic solvent may be used without limitation and the biodiesel produced by the strain may be accumulated in the hydrophobic solvent. The *Synechococcus elongatus* strain of the present disclosure excretes the produced biodiesel extracellularly and the excreted biodiesel is dissolved in the hydrophobic solvent.

In another aspect, the present disclosure provides a method for removing carbon dioxide, which includes a step of culturing the *Synechococcus elongatus* strain.

Hereinafter, the present disclosure will be described in detail through examples. However, the following examples are for illustrative purposes only and it will be apparent to those of ordinary skill in the art that the scope of the present disclosure is not limited by the examples.

[Example 1] Establishment of Strategy for Producing Fatty Acid Ethyl Ester (FAEE) from *Synechococcus elongatus* PCC7942 Strain A new metabolic pathway from pyruvate to FAEE via glycolysis was designed referring to the literature (Steen et al., 2010). After codon optimization of the DNA sequences of the pdc gene and the adh gene of *Zymomonas mobilis*, the atfA gene of *Acinetobacter* sp., the Ws2 gene of *Marinobacter hydrocarbonoclasticus* ATCC 49840 and the tesA gene of *E. coli*, the sequences were synthesized by GenScript®. *Synechococcus elongatus* as a parent strain was transformed sequentially with three modules using a module in which the pdc and adh genes were introduced at the neutral site II (NSII) (module A), a module in which the atfA or Ws2 gene was introduced at the neutral site I (NSI) (module B) and a module in which the tesA gene was introduced at the FadE deletion site (module C) (FIG. 1).

[Example 2] Construction of Strain Producing Fatty Acid Ethyl Ester (FAEE)

[Example 2-1] Construction of Vectors

Figure 2A:
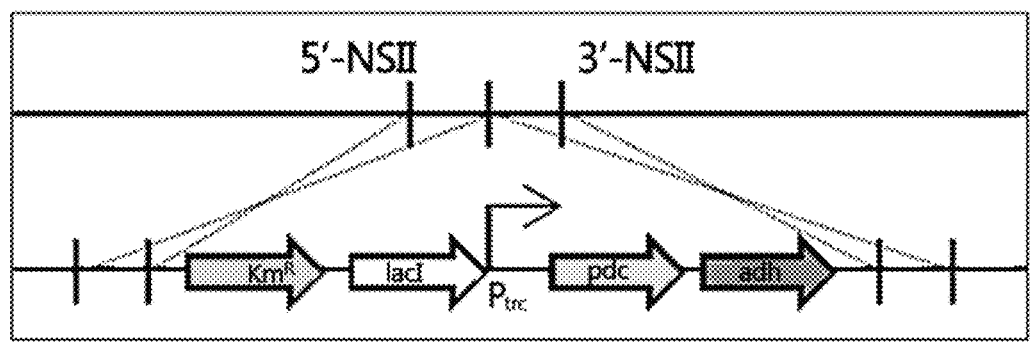
FIGS. 2A-2C are schematics of vectors (FIG. 2A: pSe2Bb1k-pdc,adh vector, FIG. 2B: pSe1Bb1s-atfA vector, FIG. 2C: pSe[FadE]Bb1c-tesA vector).

A pSe2Bb1k-GFP vector as a SyneBrick vector, a pUC57-pdc vector wherein the synthesized pdc gene was inserted and a pUC57-adh vector wherein the adh gene was inserted were prepared. In order to replace the GFP region of the SyneBrick vector with pdc and adh, respectively, GFP was removed using EcoRI/BamHI restriction enzymes and then each of the pdc and adh genes cleaved from pUC57-pdc and pUC57-adh using EcoRI/BamHI was inserted using a ligase. As a result, pSe2Bb1K-pdc and pSe2Bb1K-adh vectors were constructed. In order to insert the adh gene downstream of the pdc gene, the pSe2Bb1k-pdc vector was treated with BamHI-XhoI restriction enzymes and pSe2Bb1k-adh was treated with BglII-XhoI restriction enzymes. Then, the sequence of the adh gene was inserted downstream of the pdc gene using a ligase. As a result, a pSe2Bb1k-pdc,adh vector (first vector) was constructed (FIG. 2A).

Figure 2B:
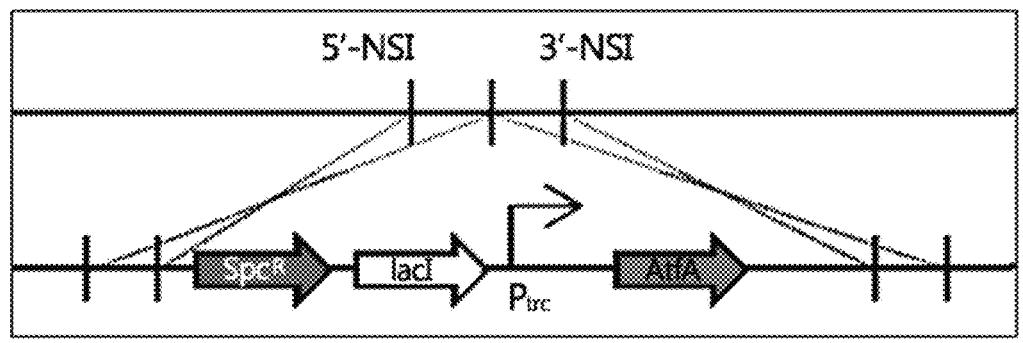

Also, a pSe1Bb1s-atfA vector and a pSe1Bb1s-Ws2 vector (second vector) was constructed by removing the GFP region of pSe1Bb1s-GFP using EcoRI-BamHI restriction enzymes and then inserting the DNA sequence of the synthesized atfA or Ws2 gene (FIG. 2B).

Figure 2C:
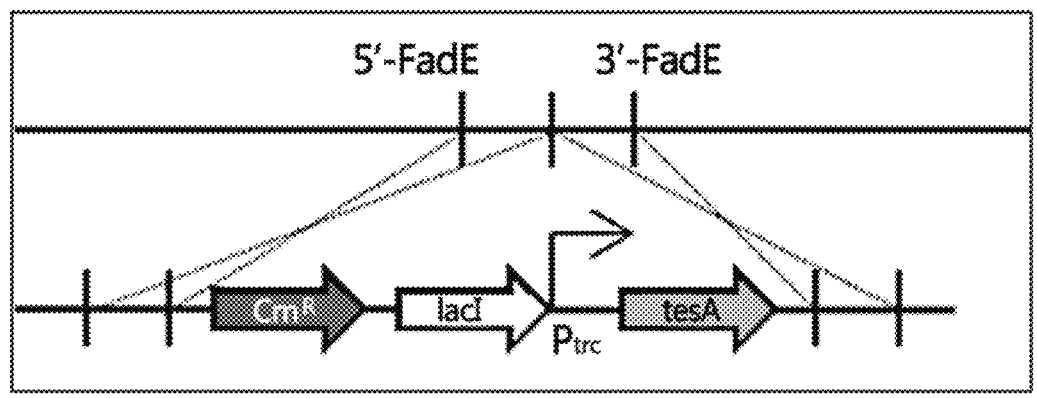

Finally, a pSe[FadE]Bb1c-tesA vector (third vector) was constructed by removing the RFP region of pSe[FadE]Bb1c-RFP using EcoRI-BamHI restriction enzymes and then inserting the DNA sequence of the synthesized tesA gene (FIG. 2C).

All the genes inserted into these vector were constructed by GeneScript®.

[Example 2-2] Construction of Transformed Strains

The constructed pSe2Bb1k-pdc,adh vector was inserted at the neutral site II of a wild-type *Synechococcus elongatus* PCC7942 strain. Then, a strain in which the modules A and B are introduced together was constructed by inserting the pSe1Bb1s-atfA or pSe1Bb1s-Ws2 vector at the neutral site I of the strain in which the module A is introduced. Finally, a biodiesel-producing strain in which the modules A, B and C are introduced together was constructed by inserting the pSe[FadE]Bb1c-tesA vector at the FadE site of the strain in which the module A and B are introduced.

[Example 3] Fatty Acid Ethyl Ester (FAEE) Production Capability of Transformed Strains In order to investigate the capability of producing biodiesel of the transformed strains constructed in Example 2, the strains were cultured under the following conditions. Specifically, 100 mL of BG-11 medium containing 10 mM MOPS buffer was added to a 100-mL bottle and then the transformed strain was added after diluting to $O.D_{730}$=0.6. Then, after adding 10 µg/mL spectinomycin, 5 µg/mL kanamycin and 5 µg/mL chloramphenicol, the strain was cultured in an incubator of 30° C. and 100 $\mu E \cdot m^{-2} \cdot s^{-1}$ while continuously supplying 5% $CO_2$. After culturing for one day, the strain was treated with 0.5 mM isopropyl β-D-1-thiogalactopyranoside (IPTG) as an inducer necessary for gene expression and with 20% hexadecane to reduce cytotoxicity by the produced fatty acid ethyl ester (FAEE). After culturing for 7 days, optical density at 730 nm and the amount of the produced fatty acid ethyl ester in the hexadecane layer were measured.

Figure 3A:
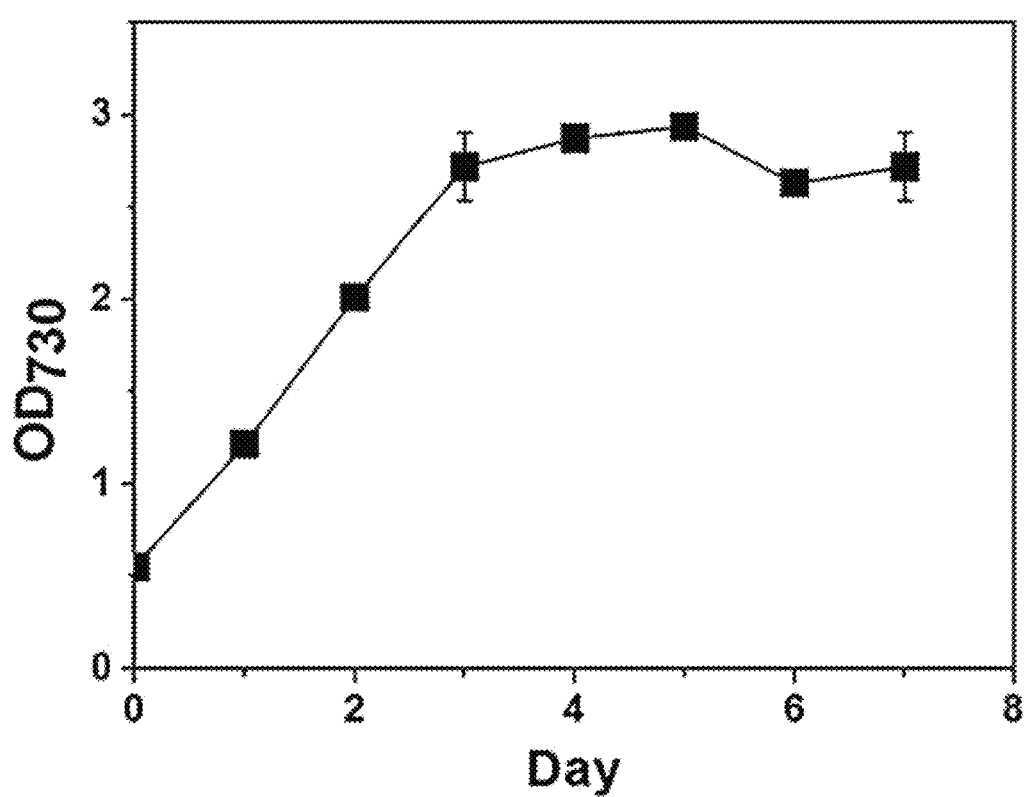
FIGS. 3A-3B show the cell growth (FIG. 3A) of and ethanol production (FIG. 3B) by a strain transformed with a pSe2Bb1k-pdc,adh vector.
Figure 3B:
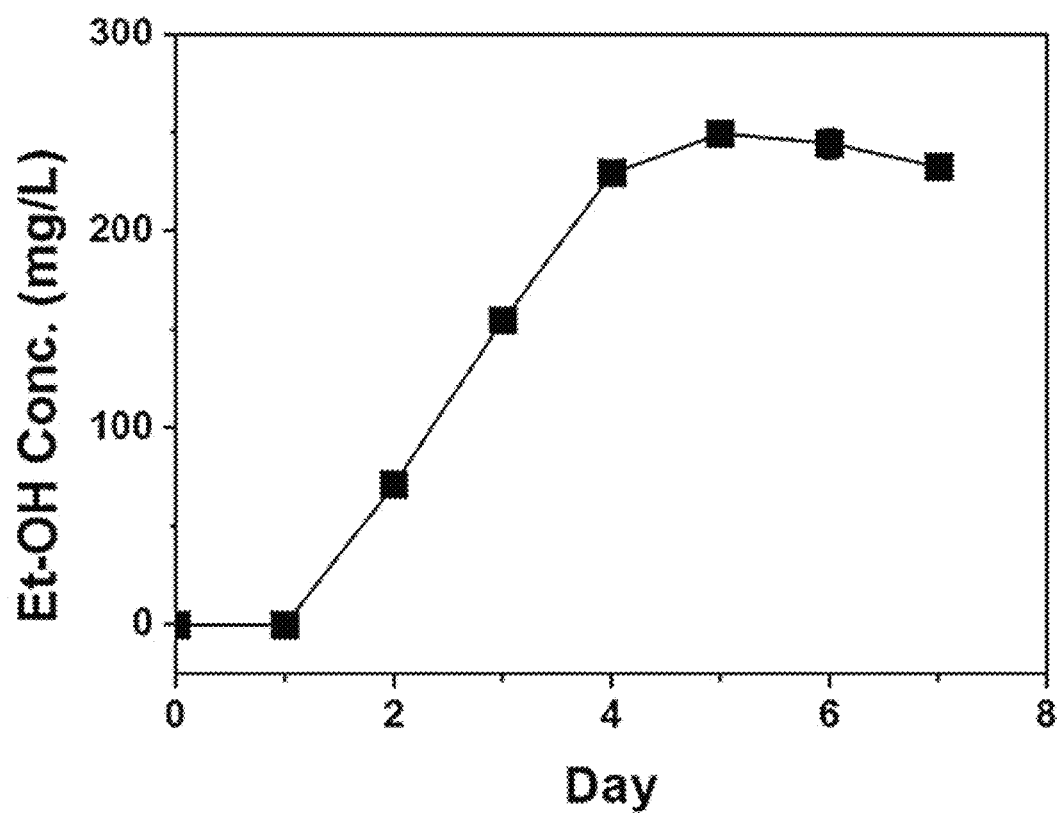
Figure 4A:
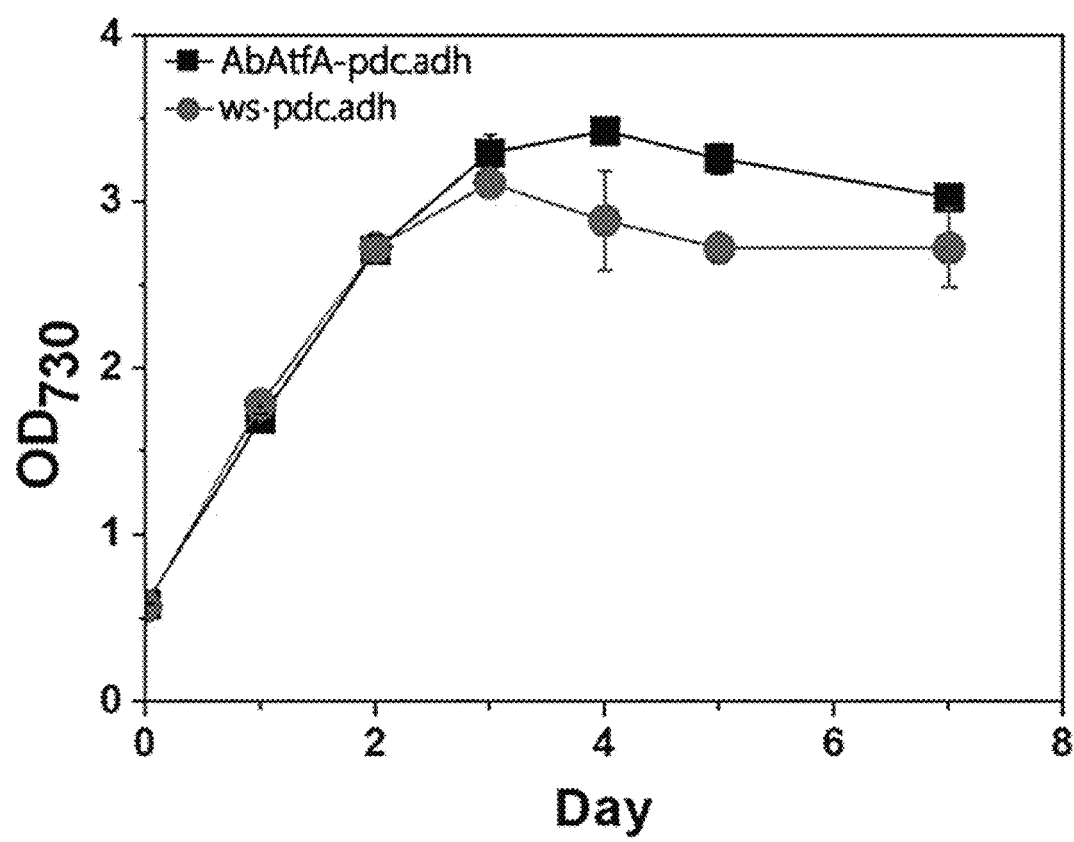
FIGS. 4A-4B show the cell growth (FIG. 4A) of and ethanol production (FIG. 4B) by a strain transformed with a pSe2Bb1k-pdc,adh vector and a pSe1Bb1s-atfA vector (indicated by squares) and a strain transformed with a pSe2Bb1k-pdc,adh vector and a pSe1Bb1s-Ws2 vector (indicated by circles).
Figure 4B:
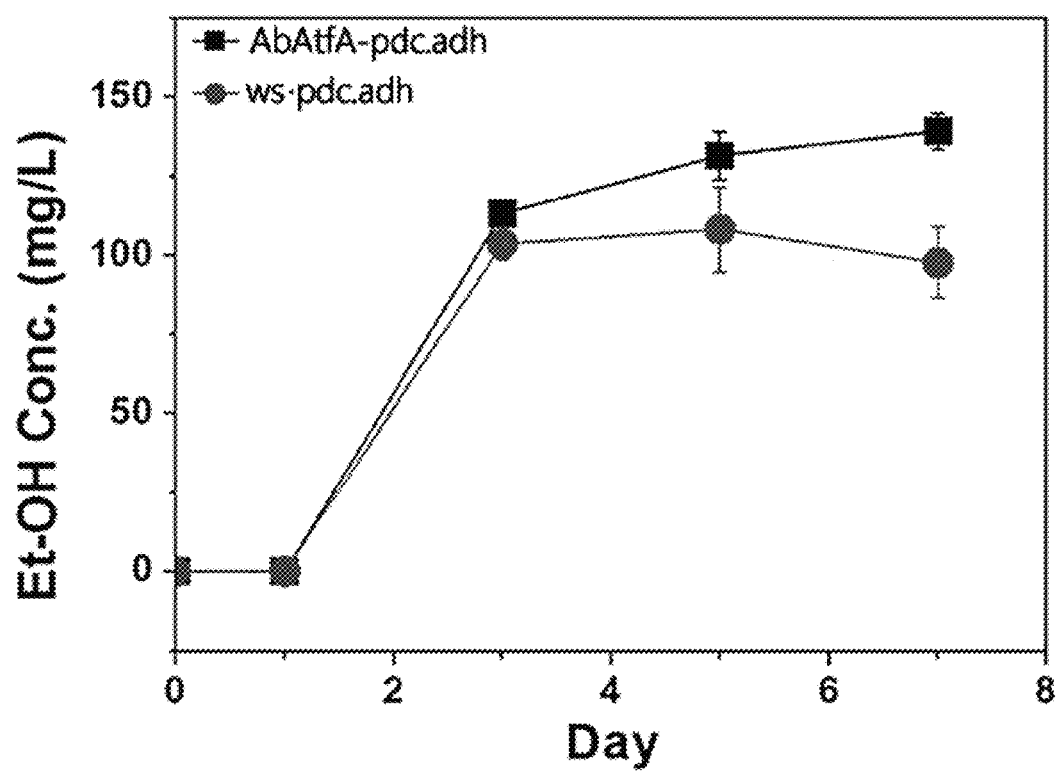
Figure 5A:
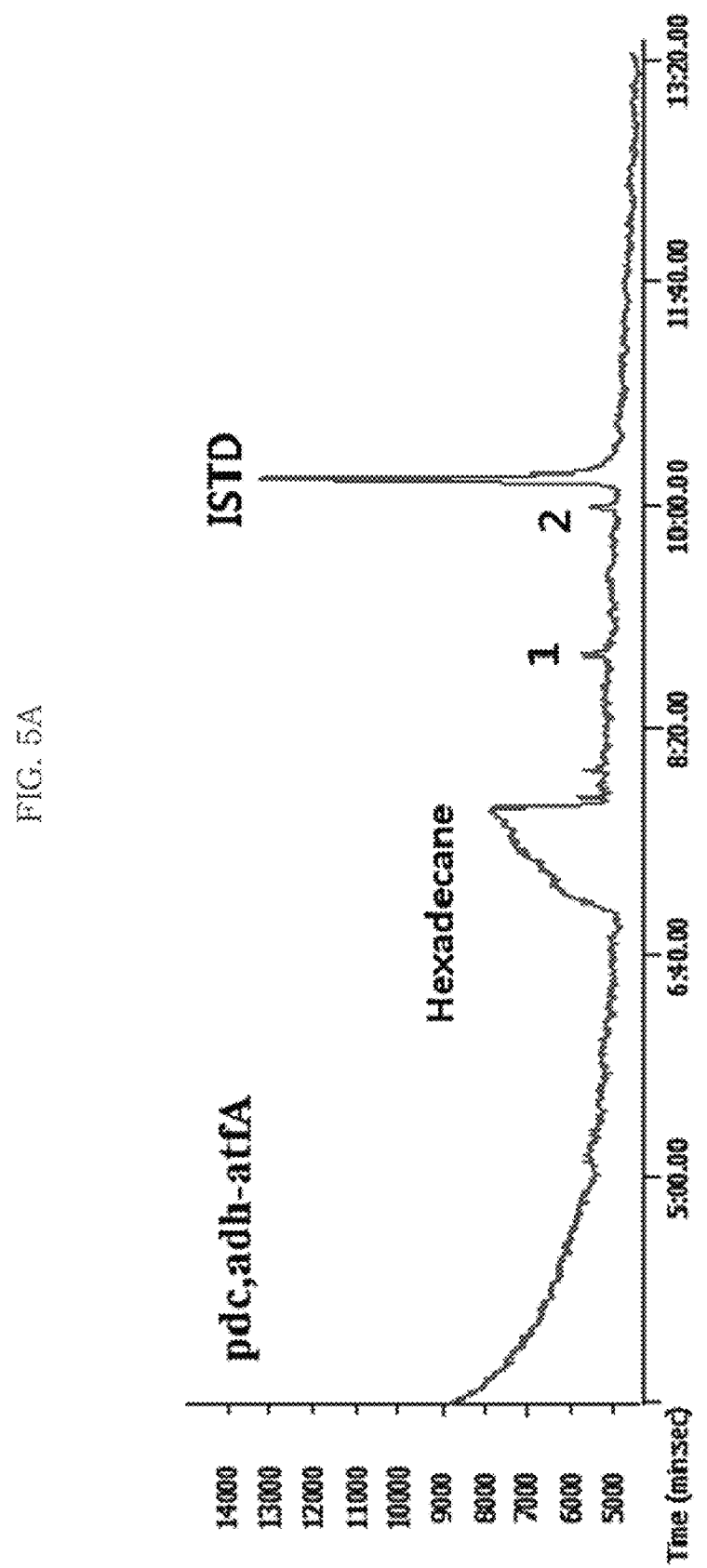
FIGS. 5A-5B show the fatty acid ethyl ester production by a strain transformed with a pSe2Bb1k-pdc,adh vector and a pSe1Bb1s-atfA vector (FIG. 5A) and a strain transformed with a pSe2Bb1k-pdc,adh vector and a pSe1Bb1s-Ws2 vector (FIG. 5B).
Figure 5B:
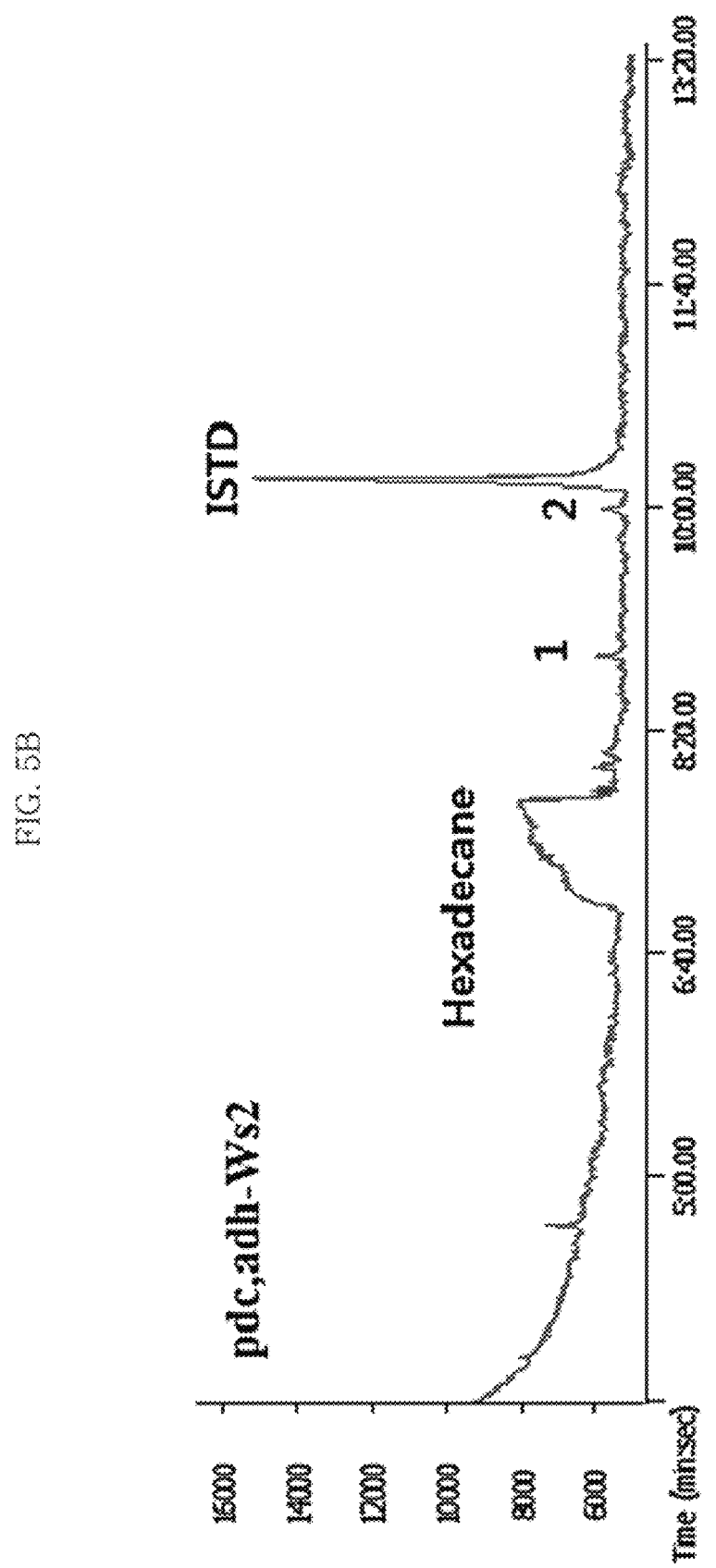
Figure 6A:
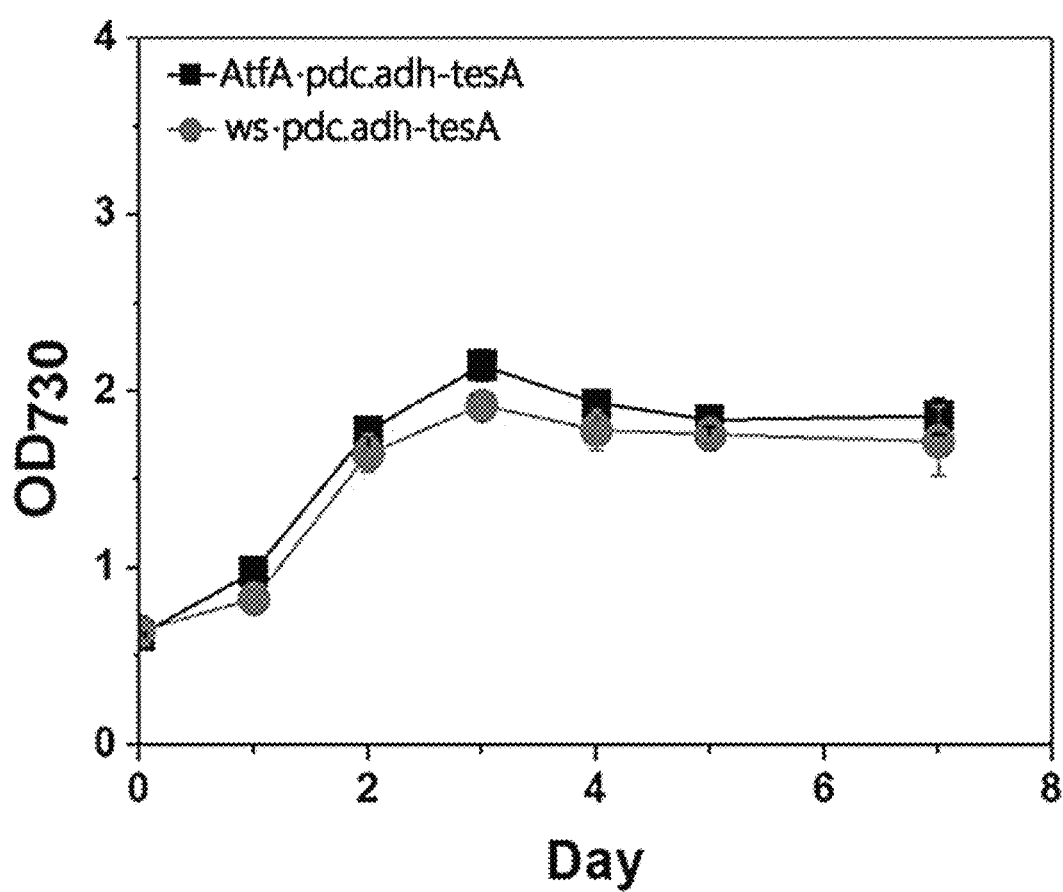
FIGS. 6A-6B show the cell growth (FIG. 6A) of and ethanol production (FIG. 6B) by a strain transformed with a pSe2Bb1k-pdc,adh vector, a pSe1Bb1s-atfA vector and a pSe[FadE]Bb1c-tesA vector (indicated by squares) and a strain transformed with a pSe2Bb1k-pdc,adh vector, a pSe1Bb1s-Ws2 vector and a pSe[FadE]Bb1c-tesA vector (indicated by circles).
Figure 6B:
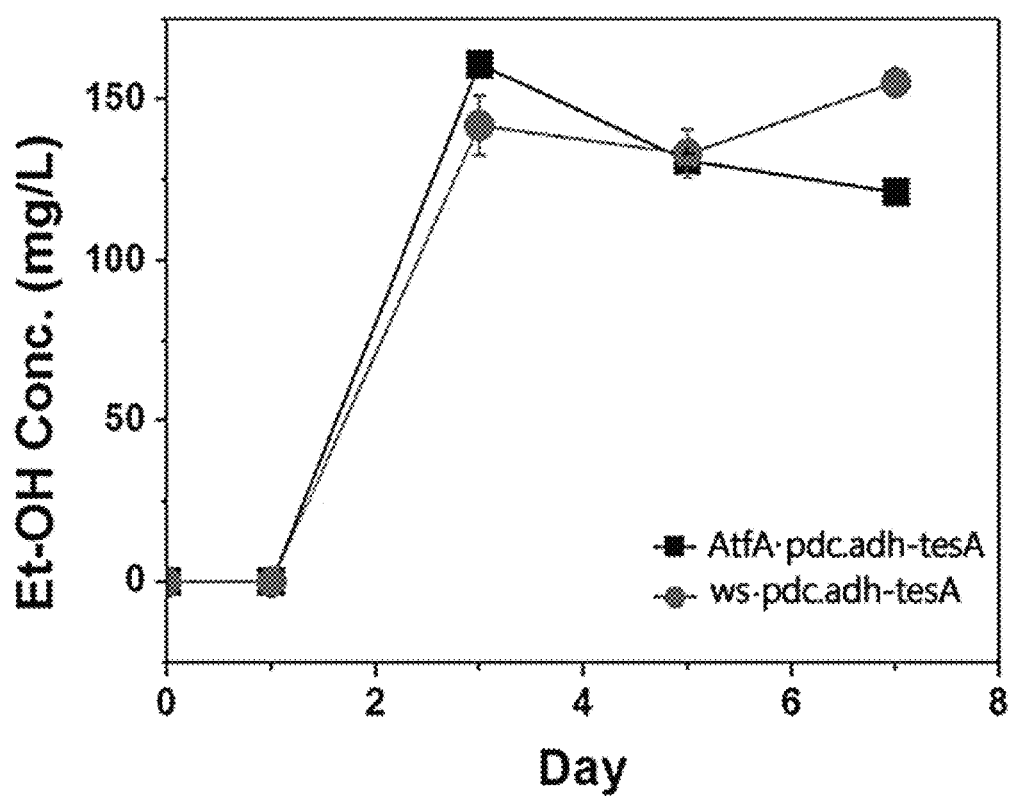
Figure 7A:
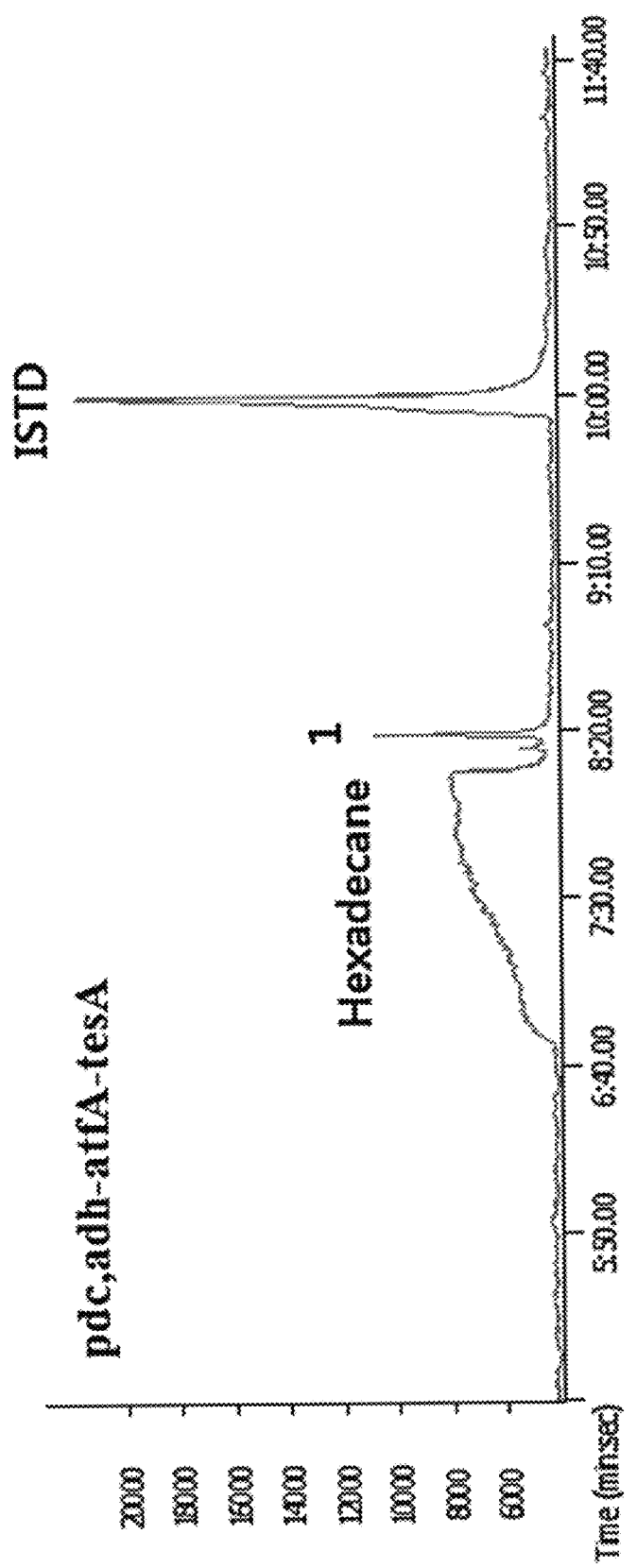
FIGS. 7A-7B show the fatty acid ethyl ester production by a strain transformed with a pSe2Bb1k-pdc,adh vector, a pSe1Bb1s-atfA vector and a pSe[FadE]Bb1c-tesA vector (FIG. 7A) and a strain transformed with a pSe2Bb1k-pdc, adh vector, a pSe1Bb1s-Ws2 vector and a pSe[FadE]Bb1c-tesA vector (FIG. 7B).
Figure 7B:
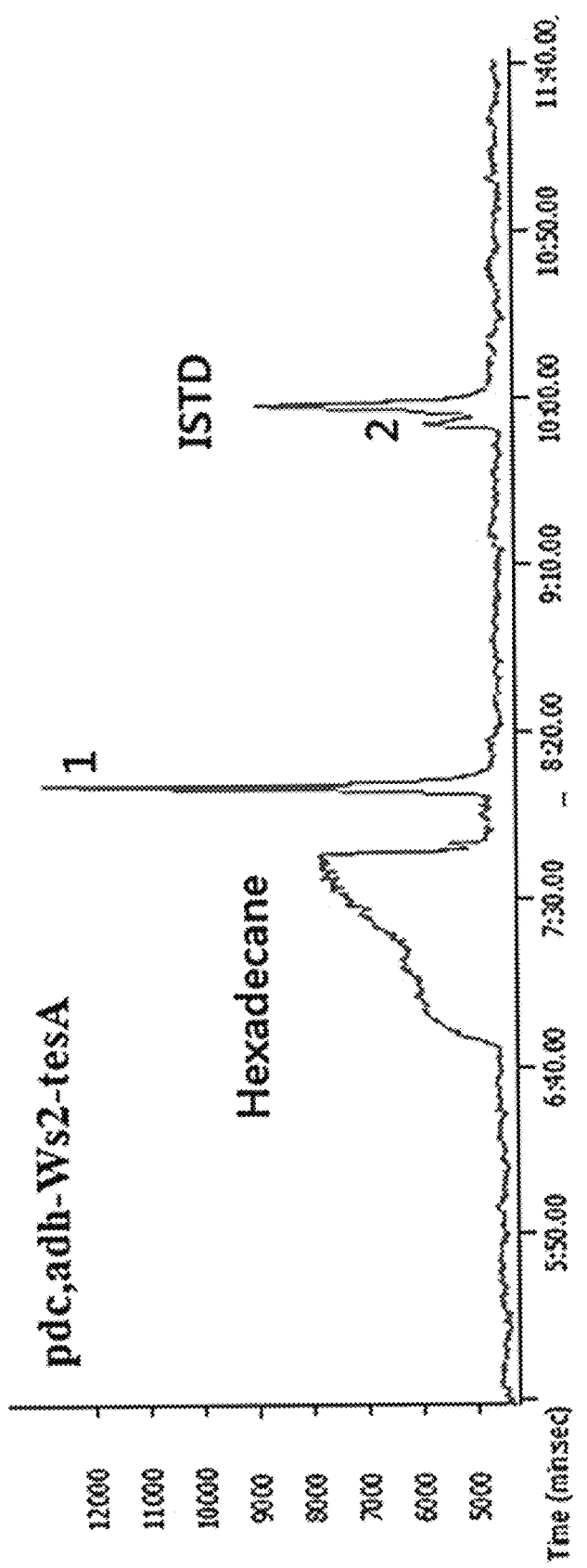

As a result, it was confirmed that up to 250 mg/L ethanol was produced by the transformed strain into which the pdc gene and the adh gene were introduced (FIG. 3B). For the strain into which the pdc, adh and atfA genes were inserted and the strain into which the pdc, adh and Ws2 genes were inserted, ethanol production was decreased at 100-150 mg/L and fatty acid ethyl ester (FAEE) peak was observed (FIGS. 4A and 4B). From mass spectroscopic analysis, the peak 1 was identified as hexadecanoic acid ethyl ester ($C_{18}H_{36}O_2$) and the peak 2 was identified as octadecanoic acid ethyl ester ($C_{20}H_{40}O_2$). Agilent 6890 and Leco's Time-Of-Flight mass spectrometer (LECO PEGASUSIII) were used for the analysis.

The hexadecanoic acid ethyl ester peak increased remarkably for the strain into which the pdc, adh, atfA and tesA genes were inserted, and both the hexadecanoic acid ethyl ester ($C_{18}H_{36}O_2$) and octadecanoic acid ethyl ester ($C_{20}H_{40}O_2$) peaks increased for the strain into which the pdc, adh, Ws2 and tesA genes were inserted.

[Accession Numbers]
Depository authority: Korea Research Institute of Bioscience and Biotechnology
Accession number: KCTC12883BP
Date of deposition: 20150827
Depository authority: Korea Research Institute of Bioscience and Biotechnology
Accession number: KCTC12884BP
Date of deposition: 20150827

What is claimed is:

1. A *Synechococcus elongatus* strain comprising: a gene encoding an enzyme which produces acetaldehyde from pyruvate; a gene encoding an enzyme which produces ethanol from acetaldehyde; and a gene encoding an enzyme which produces biodiesel from acyl-coenzyme A and ethanol, wherein the enzyme which produces acetaldehyde from pyruvate is pyruvate decarboxylase, the enzyme which produces ethanol from acetaldehyde is alcohol dehydrogenase and the enzyme which produces biodiesel from acyl-coenzyme A and ethanol is wax-ester synthase, and wherein the pyruvate decarboxylase gene comprises the nucleotide sequence of SEQ ID NO: 1, the alcohol dehydrogenase gene comprises the nucleotide sequence of SEQ ID NO: 2, and the wax-ester synthase gene comprises the nucleotide sequence of SEQ ID NO: 3 or SEQ ID NO: 4.

2. The *Synechococcus elongatus* strain according to claim 1, wherein the strain further comprises a gene encoding an enzyme which produces a free fatty acid from an acyl-acyl carrier protein (acyl-ACP), wherein the enzyme which produces a free fatty acid from an acyl-acyl carrier protein (acyl-ACP) is thioesterase, wherein the thioesterase gene comprises the nucleotide sequence of SEQ ID NO: 5.

3. The *Synechococcus elongatus* strain according to claim 1, wherein the strain is transformed with a first vector comprising a sequence derived from a pdc (pyruvate decarboxylase) gene of *Zymomonas mobilis* and a sequence derived from an adh (alcohol dehydrogenase) gene of *Zymomonas mobilis*; and a second vector comprising a sequence derived from an atfA gene of *Acinetobacter* sp. or a Ws2 gene of *Marinobacter hydrocarbonoclasticus*.

4. The *Synechococcus elongatus* strain according to claim 3, wherein the strain is further transformed with a third vector comprising a sequence derived from a tesA (thioesterase) gene of *E. coli*.

5. The *Synechococcus elongatus* strain according to claim 3, wherein the first vector is inserted at the neutral site II (NSII) of the parent strain *Synechococcus elongatus* and the second vector is inserted at the neutral site I (NSI) of the parent strain *Synechococcus elongatus*.

6. The *Synechococcus elongatus* strain according to claim 4, wherein the third vector is inserted at the FadE site of the parent strain *Synechococcus elongatus*.

7. The *Synechococcus elongatus* strain according to claim 3,
wherein the first vector comprises, in sequence, a kanamycin resistance gene, a lacI (lactose) repressor, a trc promoter, the gene encoding pyruvate decarboxylase and the gene encoding alcohol dehydrogenase; or
wherein the second vector comprises, in sequence, a spectinomycin resistance gene, a lacI repressor, a trc promoter and the gene encoding wax-ester synthase.

8. The *Synechococcus elongatus* strain according to claim 4, wherein the third vector comprises, in sequence, a chloramphenicol resistance gene, a lacI repressor, a trc promoter and the gene encoding thioesterase.

9. The *Synechococcus elongatus* strain according to claim 3, wherein the first vector comprises the nucleotide sequence of SEQ ID NO 6 and the second vector comprises the nucleotide sequence of SEQ ID NO 7 or SEQ ID NO 8.

10. The *Synechococcus elongatus* strain according to claim 4, wherein the third vector comprises the nucleotide sequence of SEQ ID NO 9.

11. The *Synechococcus elongatus* strain according to claim 4, wherein the strain transformed with the vectors is derived from the parent strain *Synechococcus elongatus* PCC7942 (ATCC 33912).

12. The *Synechococcus elongatus* strain according to claim 1, wherein the biodiesel is a fatty acid ethyl ester (FAEE).

13. The *Synechococcus elongatus* strain according to claim 1, wherein the strain is a *Synechococcus elongatus* strain with an accession number KCTC 12883BP or an accession number KCTC 12884BP.

14. The *Synechococcus elongatus* strain according to claim 1, wherein the strain absorbs and fixes carbon dioxide.

15. A method for producing biodiesel comprising culturing the *Synechococcus elongatus* strain according to claim 14.

16. A method for removing or reducing carbon dioxide comprising culturing the *Synechococcus elongatus* strain according to claim 14.

* * * * *